(12) United States Patent
Shelton, IV et al.

(10) Patent No.: US 11,992,257 B2
(45) Date of Patent: May 28, 2024

(54) ENERGIZED SURGICAL INSTRUMENT SYSTEM WITH MULTI-GENERATOR OUTPUT MONITORING

(71) Applicant: Cilag GmbH International, Zug (CH)

(72) Inventors: Frederick E. Shelton, IV, Hillsboro, OH (US); David C. Yates, West Chester, OH (US)

(73) Assignee: Cilag GmbH International, Zug (CH)

( * ) Notice: Subject to any disclaimer, the term of this patent is extended or adjusted under 35 U.S.C. 154(b) by 596 days.

(21) Appl. No.: 17/136,141

(22) Filed: Dec. 29, 2020

(65) Prior Publication Data
US 2022/0202475 A1 Jun. 30, 2022

(51) Int. Cl.
*A61B 18/14* (2006.01)
*A61B 17/32* (2006.01)
(Continued)

(52) U.S. Cl.
CPC .. *A61B 18/1445* (2013.01); *A61B 17/320068* (2013.01); *A61B 17/320092* (2013.01);
(Continued)

(58) Field of Classification Search
CPC .... A61B 17/320068; A61B 17/320092; A61B 18/1206; A61B 18/1233; A61B 18/1442; A61B 18/1445; A61B 18/16; A61B 2018/00702; A61B 2018/0072; A61B 2018/00732; A61B 2018/00767; A61B 2018/00827; A61B 2018/00845; A61B 2018/00892; A61B 2018/00994;
(Continued)

(56) References Cited

U.S. PATENT DOCUMENTS 4,184,492 A 1/1980 Meinke et al.
5,312,401 A 5/1994 Newton et al.
(Continued)

FOREIGN PATENT DOCUMENTS

EP 2926752 A2 10/2015
EP 3417797 A1 12/2018
(Continued)

OTHER PUBLICATIONS

U.S. Appl. No. 17/136,137, entitled "Filter for Monopolar Surgical Instrument Energy Path," filed Dec. 29, 2020.
(Continued)

*Primary Examiner* — Khadijeh A Vahdat
(74) *Attorney, Agent, or Firm* — Frost Brown Todd LLP

(57) ABSTRACT

A surgical system includes two instruments with corresponding end effectors that are operable to apply different types of energy to tissue of a patient. The system further includes one or more electrical power generators that are configured to generate first and second energy signals via corresponding generator outputs. A power monitor is configured to monitor a first energy parameter of the first energy signal and transmit the first energy parameter to the one or more electric power generators. The one or more electric power generators is configured to adjust a second energy parameter of the second energy signal, based at least in part on the transmitted first energy parameter, to avoid interactions between the first energy signal and the second energy signal.

20 Claims, 13 Drawing Sheets

(51) Int. Cl.
  *A61B 18/16* (2006.01)
  *A61B 34/30* (2016.01)
  A61B 18/00 (2006.01)
  A61B 18/12 (2006.01)

(52) U.S. Cl.
  CPC .............. *A61B 18/16* (2013.01); *A61B 34/30* (2016.02); *A61B 2018/00702* (2013.01); *A61B 2018/0072* (2013.01); *A61B 2018/00732* (2013.01); *A61B 2018/00767* (2013.01); *A61B 2018/00994* (2013.01); *A61B 2018/1253* (2013.01); *A61B 2018/126* (2013.01); *A61B 2018/147* (2013.01); *A61B 2018/167* (2013.01)

(58) Field of Classification Search
  CPC ...... A61B 2018/1253; A61B 2018/126; A61B 2018/1273; A61B 2018/1293; A61B 2018/147; A61B 2018/167
  See application file for complete search history.

(56) References Cited

U.S. PATENT DOCUMENTS

| | | | |
|---|---|---|---|
| 7,070,420 | B1 | 7/2006 | Wakefield et al. |
| 7,354,440 | B2 | 4/2008 | Truckai et al. |
| 7,381,209 | B2 | 6/2008 | Truckai et al. |
| 7,762,958 | B1 | 7/2010 | Webler |
| 8,663,220 | B2 | 3/2014 | Wiener et al. |
| 8,820,605 | B2 | 9/2014 | Shelton, IV |
| 9,125,662 | B2 | 9/2015 | Shelton, IV |
| 9,314,308 | B2 | 4/2016 | Parihar et al. |
| 9,949,785 | B2 | 4/2018 | Price et al. |
| 10,090,616 | B1 | 10/2018 | Leimbach et al. |
| 10,624,709 | B2 | 4/2020 | Remm |
| 10,639,038 | B2 | 5/2020 | Scott et al. |
| 10,813,640 | B2 | 10/2020 | Adams et al. |
| 10,835,307 | B2 | 11/2020 | Shelton, IV et al. |
| 10,842,523 | B2 | 11/2020 | Shelton, IV et al. |
| 2002/0128643 | A1 | 9/2002 | Simpson et al. |
| 2004/0206365 | A1 | 10/2004 | Knowlton |
| 2006/0041251 | A1 | 2/2006 | Odell et al. |
| 2006/0041252 | A1 | 2/2006 | Odell et al. |
| 2006/0079874 | A1 | 4/2006 | Faller et al. |
| 2007/0049919 | A1 | 3/2007 | Lee, Jr. et al. |
| 2007/0191713 | A1 | 8/2007 | Eichmann et al. |
| 2008/0200940 | A1 | 8/2008 | Eichmann et al. |
| 2009/0036884 | A1 | 2/2009 | Gregg et al. |
| 2010/0042097 | A1 | 2/2010 | Newton et al. |
| 2011/0034910 | A1 | 2/2011 | Ross et al. |
| 2012/0292367 | A1 | 11/2012 | Morgan et al. |
| 2013/0123783 | A1 | 5/2013 | Marczyk et al. |
| 2014/0249557 | A1 | 9/2014 | Koch, Jr. et al. |
| 2015/0313628 | A1* | 11/2015 | Allen, IV ....... A61B 17/320092 606/171 |
| 2015/0320481 | A1 | 11/2015 | Cosman, Jr. et al. |
| 2016/0143685 | A1 | 5/2016 | Friedrichs |
| 2016/0192980 | A1 | 7/2016 | Newton et al. |
| 2016/0296268 | A1 | 10/2016 | Gee et al. |
| 2017/0202591 | A1 | 7/2017 | Shelton, IV et al. |
| 2017/0202605 | A1 | 7/2017 | Shelton, IV et al. |
| 2017/0202608 | A1 | 7/2017 | Shelton, IV et al. |
| 2018/0012719 | A1 | 1/2018 | Houbre et al. |
| 2018/0078170 | A1 | 3/2018 | Panescu et al. |
| 2018/0132850 | A1 | 5/2018 | Leimbach et al. |
| 2018/0333185 | A1 | 11/2018 | Asher et al. |
| 2019/0142492 | A1 | 5/2019 | Kollmann et al. |
| 2019/0189903 | A1 | 6/2019 | Benedict et al. |
| 2019/0201047 | A1 | 7/2019 | Yates et al. |
| 2019/0201075 | A1 | 7/2019 | Shelton, IV et al. |
| 2019/0201077 | A1 | 7/2019 | Yates et al. |
| 2019/0247680 | A1 | 8/2019 | Mayer et al. |
| 2019/0290269 | A1 | 9/2019 | Shelton, IV et al. |
| 2019/0290273 | A1 | 9/2019 | Shelton, IV et al. |
| 2019/0290308 | A1 | 9/2019 | Worthington et al. |
| 2020/0069365 | A1 | 3/2020 | Harlev et al. |
| 2020/0078075 | A1* | 3/2020 | Katsuragi .............. A61B 18/10 |
| 2020/0384502 | A1 | 12/2020 | Downey et al. |
| 2021/0059709 | A1 | 3/2021 | Black et al. |

FOREIGN PATENT DOCUMENTS

| | | |
|---|---|---|
| EP | 3420918 A1 | 1/2019 |
| EP | 3461447 A1 | 4/2019 |
| EP | 3479787 A1 | 5/2019 |
| EP | 3542733 A1 | 9/2019 |
| WO | WO 1992/008417 A1 | 5/1992 |
| WO | WO 2018/165425 A1 | 9/2018 |
| WO | WO 2019/130111 A1 | 7/2019 |
| WO | WO 2020/051462 A1 | 3/2020 |

OTHER PUBLICATIONS

U.S. Appl. No. 17/136,139, entitled "Electrosurgical Instrument System with Parasitic Energy Loss Monitor," filed Dec. 29, 2020.
U.S. Appl. No. 17/136,145, entitled "Electrosurgical Instrument with Shaft Voltage Monitor," filed Dec. 29, 2020.
U.S. Appl. No. 17/136,154, entitled "Electrosurgical Instrument with Electrical Resistance Monitor at Rotary Coupling," filed Dec. 29, 2020.
U.S. Appl. No. 17/136,158, entitled "Electrosurgical Instrument with Modular Component Contact Monitoring," filed Dec. 29, 2020.
International Search Report and Written Opinion dated May 17, 2022, for International Application No. PCT/IB2021/062411, 20 pages.
International Search Report and Written Opinion dated Mar. 22, 2022, for International Application No. PCT/IB2021/062413, 13 pages.
International Search Report and Written Opinion dated Mar. 24, 2022, for International Application No. PCT/IB2021/062414, 17 pages.
International Search Report and Written Opinion dated Mar. 24, 2022, for International Application No. PCT/IB2021/062416, 16 pages.
International Search Report and Written Opinion dated Mar. 30, 2022, for International Application No. PCT/IB2021/062417, 17 pages.
International Search Report and Written Opinion dated Apr. 7, 2022, for International Application No. PCT/IB2021/062418, 13 pages.

* cited by examiner

ENERGIZED SURGICAL INSTRUMENT SYSTEM WITH MULTI-GENERATOR OUTPUT MONITORING

BACKGROUND

A variety of ultrasonic surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein, in its entirety; U.S. Pub. No. 2007/0191713, entitled "Ultrasonic Device for Cutting and Coagulating," published Aug. 16, 2007, now abandoned, the disclosure of which is incorporated by reference herein, in its entirety; and U.S. Pub. No. 2008/0200940, entitled "Ultrasonic Device for Cutting and Coagulating," published Aug. 21, 2008, now abandoned, the disclosure of which is incorporated by reference herein, in its entirety.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein, in its entirety; U.S. Pat. No. 7,381,209, entitled "Electrosurgical Instrument," issued Jun. 3, 2008, the disclosure of which is incorporated by reference herein, in its entirety.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein, in its entirety; and U.S. Pat. No. 8,663,220, entitled "Ultrasonic Electrosurgical Instruments," issued Mar. 4, 2014, the disclosure of which is incorporated by reference herein, in its entirety.

In some scenarios, it may be preferable to have surgical instalments grasped and manipulated directly by the hand or hands of one or more human operators. In addition, or as an alternative, it may be preferable to have surgical instalments controlled via a robotic surgical system. Examples of robotic surgical systems and associated instrumentation are disclosed in U.S. Pat. No. 10,624,709, entitled "Robotic Surgical Tool with Manual Release Lever," issued Apr. 21, 2020, the disclosure of which is incorporated by reference herein, in its entirety; U.S. Pat. No. 9,314,308, entitled "Robotic Ultrasonic Surgical Device With Articulating End Effector," issued on Apr. 19, 2016, the disclosure of which is incorporated by reference herein, in its entirety; U.S. Pat. No. 9,125,662, entitled "Multi-Axis Articulating and Rotating Surgical Tools," issued Sep. 8, 2015, the disclosure of which is incorporated by reference herein, in its entirety; U.S. Pat. No. 8,820,605, entitled "Robotically-Controlled Surgical Instruments," issued Sep. 2, 2014, the disclosure of which is incorporated by reference herein, in its entirety; US. Pub. No. 2019/0201077, entitled "Interruption of Energy Due to Inadvertent Capacitive Coupling," published Jul. 4, 2019, issued as U.S. Pat. No. 11,291,495 on Apr. 5, 2022, the disclosure of which is incorporated by reference herein, in its entirety; U S. Pub. No. 2012/0292367, entitled "Robotically-Controlled End Effector," published on Nov. 11, 2012, now abandoned, the disclosure of which is incorporated by reference herein, in its entirety; and U.S. patent application Ser. No. 16/556,661, entitled "Ultrasonic Surgical Instalment with a Multi-Planar Articulating Shaft Assembly," filed on Aug. 30, 2019, issued as U.S. Pat. No. 11,690,642 on Jul. 4, 2023 the disclosure of which is incorporated by reference herein, in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
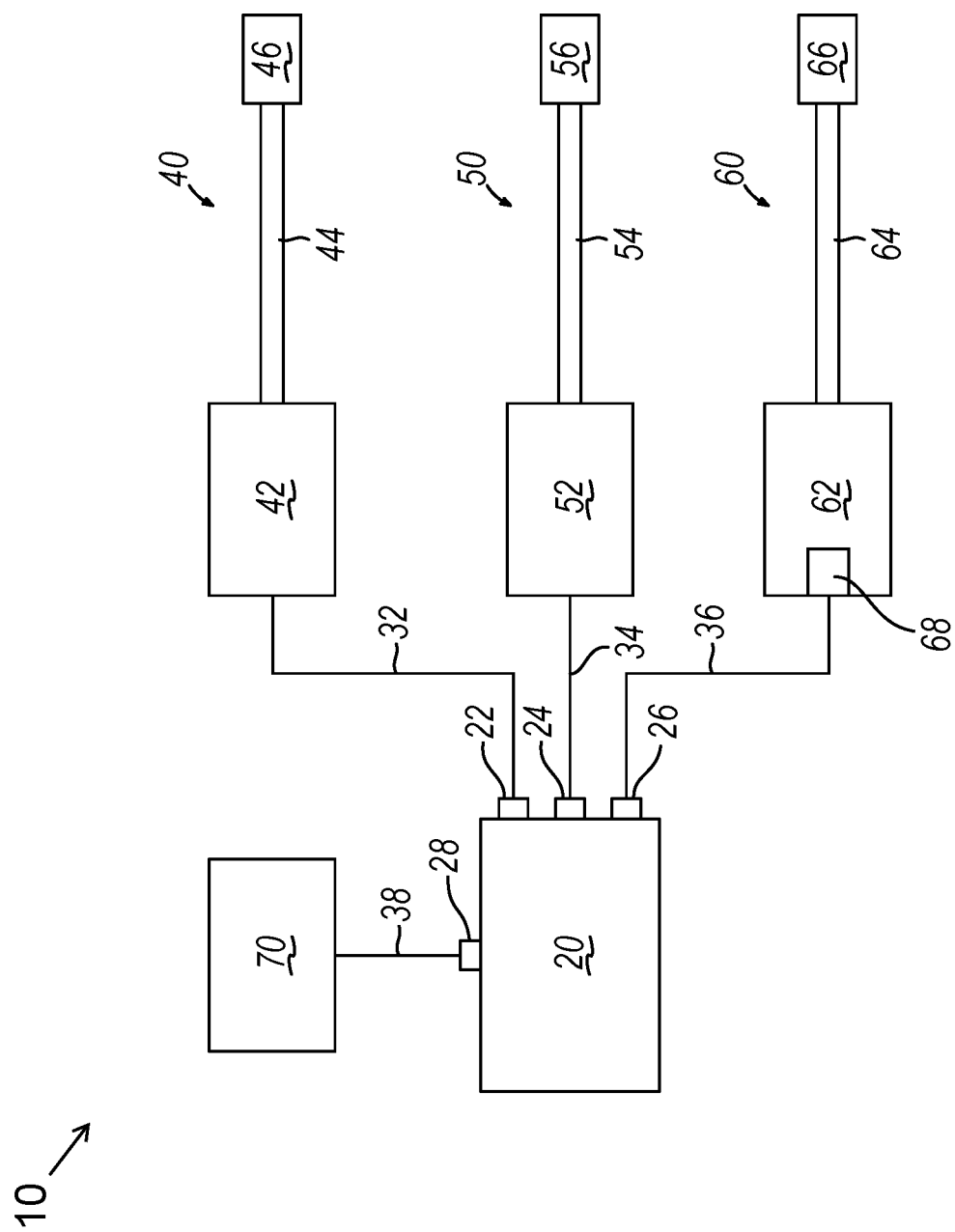
FIG. 1 depicts a schematic view of an example of a robotic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "top," "bottom," "above," and "below," are used with respect to the examples and associated figures and are not intended to unnecessarily limit the invention described herein.

I. Example of a Robotic Surgical System

As noted above, in some surgical procedures, it may be desirable to utilize a robotically controlled surgical system. Such a robotically controlled surgical system may include one or more surgical instruments that are controlled and driven robotically via one or more users that are either in the same operating room or remote from the operating room. FIG. 1 illustrates on example of various components that may be incorporated into a robotic surgical system (10). System (10) of this example includes a console (20), a monopolar RF electrosurgical instrument (40), a bipolar RF electrosurgical instrument (50), and an ultrasonic surgical instrument (60). While FIG. 1 shows all three instruments (40, 50, 60) coupled with console (20) at the same time, there may be usage scenarios where only one or two of instruments (40, 50, 60) coupled with console (20) at the same time. In addition, there may be usage scenarios where various other instruments are coupled with console (20) in addition, or as an alternative to, one or more of instruments (40, 50, 60) being coupled with console (20).

Monopolar RF electrosurgical instrument (40) of the present example includes a body (42), a shaft (44) extending distally from body (42), and an end effector (46) at the distal end of shaft (44). Body (42) is configured to couple with a robotic arm (not shown in FIG. 1) of system (10), such that the robotic arm is operable to position and orient monopolar RF electrosurgical instrument (40) in relation to a patient. In versions where monopolar RF electrosurgical instrument (40) includes one or more mechanically driven components (e.g., jaws at end effector (46), articulating sections of shaft (44), rotating sections of shaft (44), etc.), body (42) may include various components that are operable to convert one or more mechanical drive inputs from the robotic arm into motion of the one or more mechanically driven components of monopolar RF electrosurgical instrument (40).

As also shown in FIG. 1, body (42) is coupled with a corresponding port (22) of console (20) via a cable (32). Console (20) is operable to provide electrical power to monopolar RF electrosurgical instrument (40) via port (22) and cable (32). In some versions, port (22) is dedicated to driving monopolar RF electrosurgical instruments like monopolar RF electrosurgical instrument (40). In some other versions, port (22) is operable to drive various kinds of instruments (e.g., including instruments (50, 60), etc.). In some such versions, console (20) is operable to automatically detect the kind of instrument (40, 50, 60) that is coupled with port (22) and adjust the power profile to port (22) accordingly. In addition, or in the alternative, console (20) may adjust the power profile to port (22) based on a selection made by an operator via console (20), manually identifying the kind of instrument (40, 50, 60) that is coupled with port (22).

Shaft (44) is operable to support end effector (46) and provides one or more wires or other paths for electrical communication between base (42) and end effector (46). Shaft (44) is thus operable to transmit electrical power from console (20) to end effector (46). Shaft (44) may also include various kinds of mechanically movable components, including but not limited to rotating segments, articulating sections, and/or other kinds of mechanically movable components as will be apparent to those skilled in the art in view of the teachings herein.

End effector (46) of the present example includes an electrode that is operable to apply monopolar RF energy to tissue. Such an electrode may be incorporated into a sharp blade, a needle, a flat surface, some other atraumatic structure, or any other suitable kind of structure as will be apparent to those skilled in the art in view of the teachings herein. End effector (46) may also include various other kinds of components, including but not limited to grasping jaws, etc.

System (10) of this example further includes a ground pad (70) that is coupled with a corresponding port (28) of console (20) via a cable (38). In some versions, ground pad (70) is incorporated into a patch or other structure that is adhered to the skin of the patient (e.g., on the thigh of the patient). In some other versions, ground pad (70) is placed under the patient (e.g., between the patient and the operating table). In either case, ground pad (70) may serve as a return path for monopolar RF energy that is applied to the patient via end effector (46). In some versions, port (28) is a dedicated ground return port. In some other versions, port (28) is a multi-purpose port that is either automatically designated as a ground return port upon console (20) detecting the coupling of ground pad (70) with port (28) or manually designated as a ground return port via an operator using a user input feature of console (20).

Bipolar RF electrosurgical instrument (50) of the present example includes a body (52), a shaft (54) extending distally from body (52), and an end effector (56) at the distal end of shaft (54). Each of these components (52, 54, 56) may be configured and operable in accordance with the above description of corresponding components (42, 44, 46) of monopolar RF electrosurgical instrument (50), except that end effector (56) of this example is operable to apply bipolar RF energy to tissue. Thus, end effector (56) includes at least two electrodes, with those two electrodes being configured to cooperate with each other to apply bipolar RF energy to tissue. Bipolar RF electrosurgical instrument (50) is coupled with console (20) via a cable (34), which is further coupled with a port (24) of console (20). Port (24) may be dedicated to powering bipolar RF electrosurgical instruments. Alternatively, port (24) or may be a multi-purpose port whose output is determined based on either automatic detection of bipolar RF electrosurgical instrument (50) or operator selection via a user input feature of console (20).

Ultrasonic surgical instrument (60) of the present example includes a body (62), a shaft (64) extending distally from body (62), and an end effector (66) at the distal end of shaft (64). Each of these components (62, 64, 66) may be configured and operable in accordance with the above description of corresponding components (42, 44, 46) of monopolar RF electrosurgical instrument (50), except that end effector (66) of this example is operable to apply ultrasonic energy to tissue. Thus, end effector (66) includes an ultrasonic blade or other ultrasonically vibrating element. In addition, base (62) includes an ultrasonic transducer (68) that is operable to generate ultrasonic vibrations in response to electrical power, while shaft (64) includes an acoustic waveguide that is operable to communicate the ultrasonic vibrations from transducer (68) to end effector (66).

Ultrasonic surgical instrument (60) is coupled with console (20) via a cable (36), which is further coupled with a port (26) of console (20). Port (26) may be dedicated to powering ultrasonic electrosurgical instruments. Alternatively, port (26) or may be a multi-purpose port whose output is determined based on either automatic detection of ultrasonic instrument (60) or operator selection via a user input feature of console (20).

While FIG. 1 shows monopolar RF, bipolar RF, and ultrasonic capabilities being provided via three separate, dedicated instalments (40, 50, 60), some versions may include an instrument that is operable to apply two or more of monopolar RF, bipolar RF, or ultrasonic energy to tissue. In other words, two or more of such energy modalities may be incorporated into a single instrument. Examples of how such different modalities may be integrated into a single instalment are described in U S. Pub. No. 2017/0202591, entitled "Modular Battery Powered Handheld Surgical Instrument with Selective Application of Energy Based on Tissue Characterization," published Jul. 20, 2017, issued as U.S. Pat. No. 11,229,471 on Jan. 25, 2022, the disclosure of which is incorporated by reference herein, in its entirety. Other examples will be apparent to those skilled in the art in view of the teachings herein.

Figure 2:
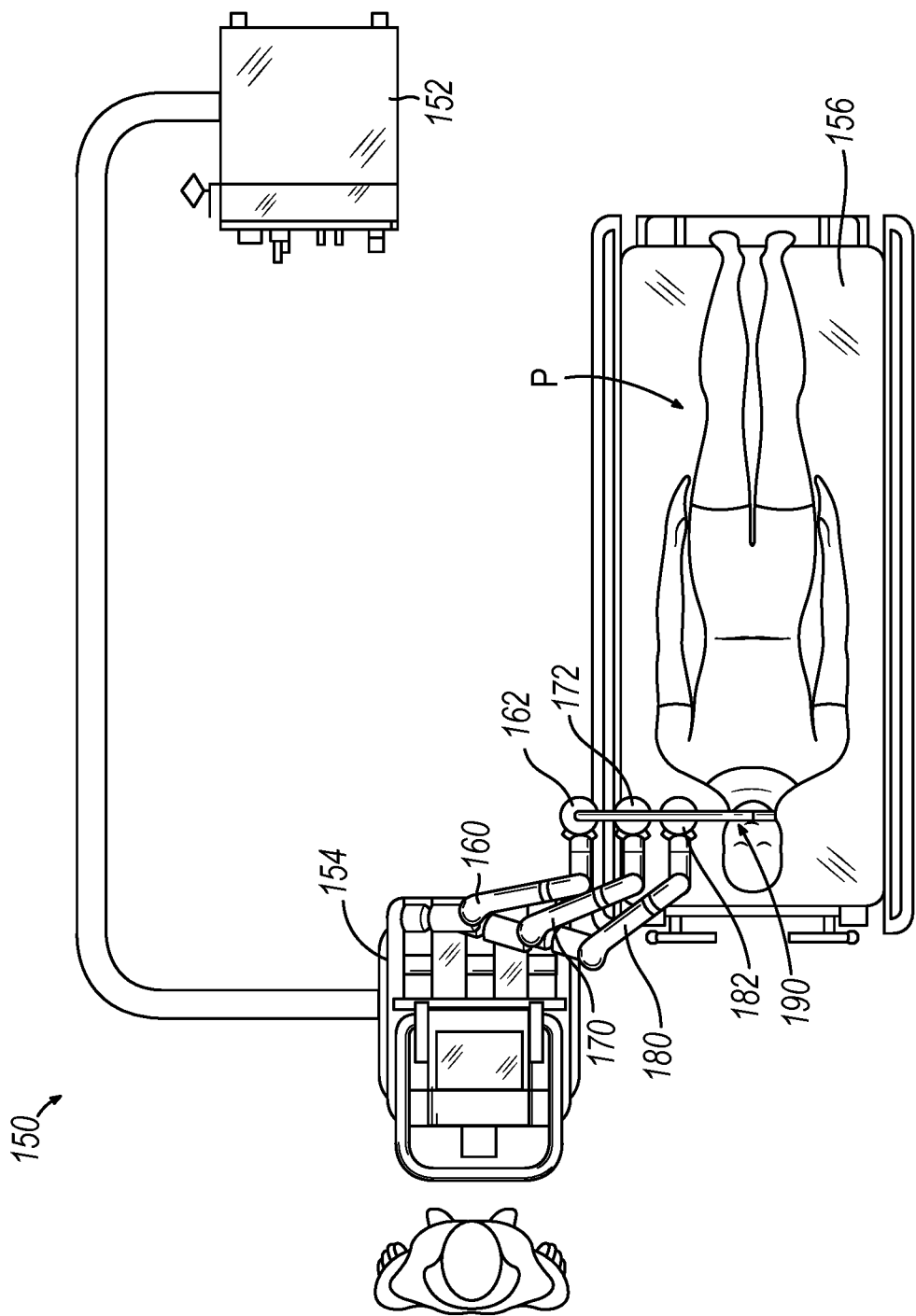
FIG. 2 depicts a schematic view of an example of a robotic surgical system being used in relation to a patient.

FIG. 2 shows an example of a robotic surgical system (150) in relation to a patient (P) on a table (156). System (150) of this example includes a control console (152) and a drive console (154). Console (152) is operable to receive user inputs from an operator; while drive console (154) is operable to convert those user inputs into motion of a set of robotic arms (160, 170, 180). In some versions, consoles (152, 154) collectively form an equivalent to console (20) described above. While consoles (152, 154) are shown as separate units in this example, consoles (152, 154) may in fact be combined as a single unit in some other examples.

Robotic arms (160, 170, 180) extend from drive console (154) in this example. In some other versions, robotic arms (160, 170, 180) are integrated into table (156) or some other structure. Each robotic arm (160, 170, 180) has a corresponding drive interface (162, 172, 182). In this example, three drive interfaces (162, 172, 182) are coupled with one single instrument assembly (190). In some other scenarios, each drive interface (162, 172, 182) is coupled with a separate respective instrument. By way of example only, a drive interface (162, 172, 182) may couple with a body of an instrument, like bodies (42, 52, 62) of instruments (40, 50, 60) described above. In any case, robotic arms (160, 170, 180) may be operable to move instrument (40, 50, 60, 190) in relation to the patient (P) and actuate any mechanically driven components of instrument (40, 50, 60, 190). Robotic arms (160, 170, 180) may also include features that provide a pathway for communication of electrical power to instrument (40, 50, 60, 190). For instance, cables (32, 34, 36) may be at least partially integrated into robotic arms (160, 170, 180). In some other versions, robotic arms (160, 170, 180) may include features to secure but not necessarily integrate cables (32, 34, 36). As yet another variation, cables (32, 34, 36) may simply stay separate from robotic arms (160, 170, 180). Other suitable features and arrangements that may be used to form robotic surgical systems (10, 150) will be apparent to those skilled in the art in view of the teachings herein.

In robotic surgical systems like robotic surgical systems (10, 150), each port (22, 24, 26, 28) may have a plurality of electrical features providing inputs and outputs between console (20, 152) and robotic arms (160, 170, 180) and/or instruments (40, 50, 60, 190). These electrical features may include sockets, pins, contacts, or various other features that are in close proximity with each other. In some scenarios, this proximity may provide a risk of power or signals undesirably crossing from one electrical feature to another electrical feature, which may cause equipment failure, equipment damage, sensor errors, and/or other undesirable results. In addition, or in the alternative, this proximity may provide a risk of generating electrical potentials between proximate components or creating capacitive couplings between electrical features. Such capacitive coupling may provide undesirable results such as power reductions, signal reductions, signal interference, patient injuries, and/or other undesirable results. It may therefore be desirable to provide features to prevent or otherwise address such occurrences at ports (22, 24, 26, 28).

Similarly, each robotic arm (160, 170, 180), each cable (32, 34, 36, 38), and/or each instrument (40, 50, 60, 190) may include a plurality of wires, traces in rigid or flexible circuits, and other electrical features that are in close proximity with each other. Such electrical features may also be in close proximity with other components that are not intended to provide pathways for electrical communication but are nevertheless formed of an electrically conductive material. Such electrically conductive mechanical features may include moving components (e.g., drive cables, drive bands, gears, etc.) or stationary components (e.g., chassis or frame members, etc.). This proximity may provide a risk of power or signals undesirably crossing from one electrical feature to another electrical feature and/or from one electrical feature to an electrically conductive mechanical feature, which may cause equipment failure, equipment damage, sensor errors, and/or other undesirable results. In addition, or in the alternative, this proximity may provide a risk of generating electrical potentials between proximate components or creating capacitive couplings between electrical features and/or between an electrical feature and an electrically conductive mechanical feature. Such capacitive coupling may provide undesirable results such as power reductions, signal reductions, signal interference, patient injuries, and/or other undesirable results. It may therefore be desirable to provide features to prevent or otherwise address such occurrences within robotic arms (160, 170, 180), within cables (32, 34, 36, 38), and/or within instruments (40, 50, 60, 190).

II. Example of Handheld Surgical Instrument

Figure 3:
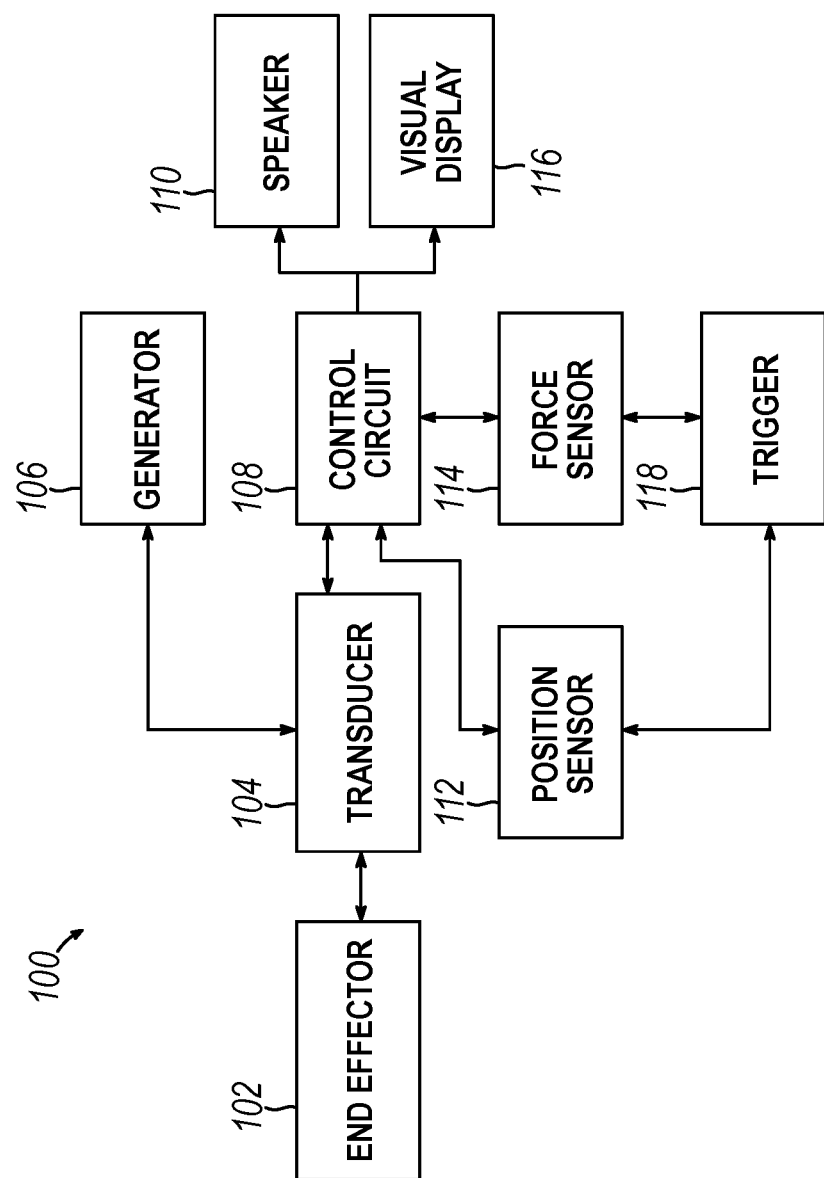
FIG. 3 depicts a schematic view of examples of components that may be incorporated into a surgical instrument.

In some procedures, an operator may prefer to use a handheld surgical instalment in addition to, or in lieu of, using a robotic surgical system (10, 150). FIG. 3 illustrates an example of various components that may be integrated into a handheld surgical instrument (100). In addition to the following teachings, instalment (200) may be constructed and operable in accordance with at least some of the teachings of U.S. Pub. No. 2017/0202608, entitled "Modular Battery Powered Handheld Surgical Instrument Containing Elongated Multi-Layered Shaft," published Jul. 20, 2017, issued as U.S. Pat. No. 10,835,307 on Nov. 17, 2020, the disclosure of which is incorporated by reference herein, in its entirety; and/or various other references cited herein. Instalment (100) of this example includes an end effector (102), an ultrasonic transducer (104), a power generator (106), a control circuit (108), a speaker (110), a position sensor (112), a force sensor (114), a visual display (116), and a trigger (118). In some versions, end effector (102) is disposed at a distal end of a shaft (not shown in FIG. 3), while the other components (104, 106, 108, 110, 112, 114, 116, 118) are incorporated into a handle assembly (not shown in FIG. 3) at the proximal end of the shaft. Some variations may also provide some of components (104, 106, 108, 110, 112, 114, 116, 118) in a separate piece of capital equipment. For instance, power generator (106), speaker (110), and/or visual display (116) may be incorporated into a separate piece of capital equipment that is coupled with instalment (100).

End effector (102) may be configured and operable like end effectors (46, 56, 66) described above, such that end effector (102) may be operable to apply monopolar RF energy, bipolar RF energy, or ultrasonic energy to tissue. Transducer (104) may be configured and operable like transducer (68). Generator (106) may be operable to provide electrical power as needed to drive transducer (68) and/or to provide RF energy via end effector (102). In versions where generator (106) is integrated into a handle assembly of instrument (106), generator (106) may comprise one or more battery cells, etc. Control circuit (108) may include one or more microprocessors and/or various other circuitry components that may be configured to provide signal processing and other electronic aspects of operability of instrument (100). Position sensor (112) may be configured to sense the position and/or orientation of instrument (102). In some versions, control circuit (108) is configured to vary the operability of instrument (102) based on data from position sensor (112). Force sensor (114) is operable to sense one or more force parameters associated with usage of instrument (100). Such force parameters may include force being applied to instrument (100) by the operator, force applied to tissue by end effector (102), or other force parameters as will be apparent to those skilled in the art in view of the teachings herein. In some versions, control circuit (108) is configured to vary the operability of instrument (102) based on data from force sensor (114). In some versions, one or both of sensors (112, 114) may be incorporated into end effector (102). In addition, or in the alternative, one or both of sensors (112, 114) may be incorporated into a shaft assembly (not shown) of instrument (100). Variations of instrument (100) may also incorporate various other kinds of sensors (e.g., in addition to or in lieu of sensors (112, 114) in end effector (102), in the shaft assembly, and/or elsewhere within instrument (100).

Trigger (118) is operable to control an aspect of operation of end effector (102), such as movement of a pivoting jaw, translation of a cutting blade, etc. Speaker (110) and visual display (116) are operable to provide audible and visual feedback to the operator relating to operation of instrument (100). The above-described components (102, 104, 106, 108, 110, 112, 114, 116, 118) of instrument (100) are illustrative examples, such that components (102, 104, 106, 108, 110, 112, 114, 116, 118) may be varied, substituted, supplemented, or omitted as desired.

Figure 4:
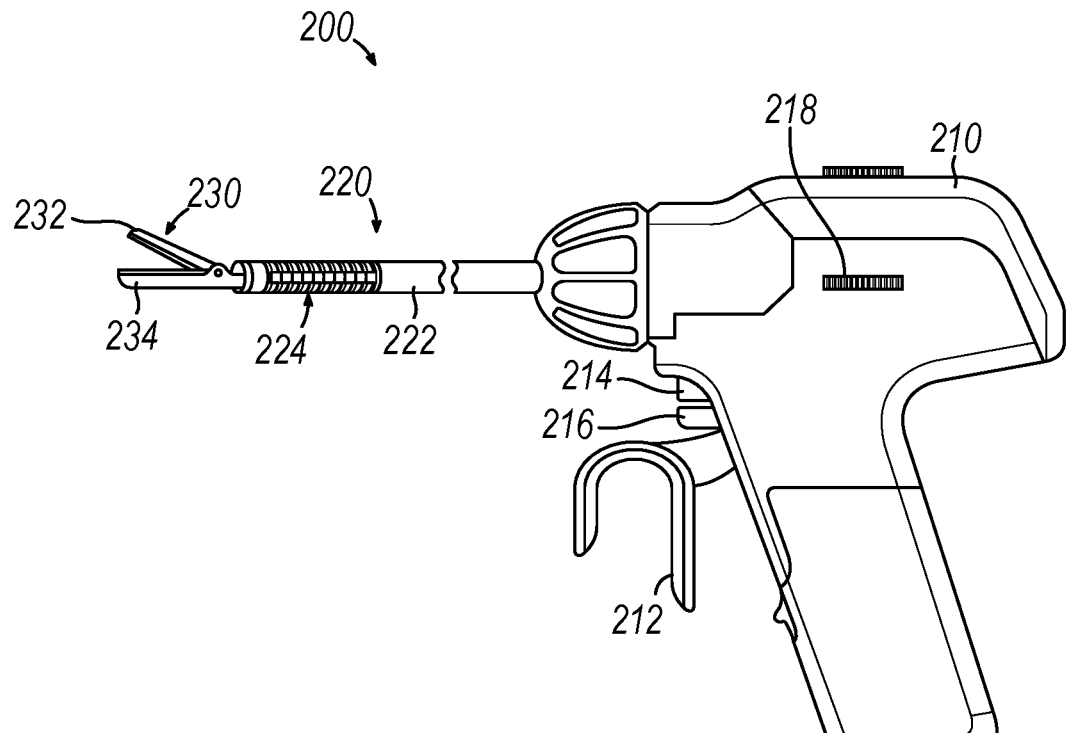
FIG. 4 depicts a side elevation view of an example of a handheld surgical instrument.

FIG. 4 shows an example of a form that instrument (100) may take. In particular, FIG. 4 shows a handheld instalment (200). In addition to the following teachings, instrument (200) may be constructed and operable in accordance with at least some of the teachings of U.S. Pub. No. 2017/0202591, now U.S. Pat. No. 11,229,471, the disclosure of which is incorporated by reference herein, in its entirety; and/or various other references cited herein. In the present example, instalment (200) includes a handle assembly (210), a shaft assembly (220), and an end effector (230). Handle assembly (210) includes a pivoting trigger (212), a first trigger button (214), a second trigger button (216), and an articulation control (218). Shaft assembly (220) includes a rigid shaft portion (222) and an articulation section (224). End effector (230) is distal to articulation section (224) and includes an upper jaw (232) and a lower jaw (234).

By way of example only, handle assembly (210) may include one or more of the above-described components (104, 106, 108, 110, 112, 114, 116, 118). Trigger (212) may be operable to drive upper jaw (232) to pivot toward lower jaw (234) (e.g., to grasp tissue between haws (232, 234)). Trigger buttons (214, 216) may be operable to activate delivery of energy (e.g., RF energy and/or ultrasonic energy) via end effector (230). Articulation control (218) is operable to drive deflection of shaft assembly (220) at articulation section (224), thereby driving lateral deflection of end effector (230) away from or toward the central longitudinal axis defined by rigid shaft portion (222). End effector (230) may include one or more electrodes that is/are operable to apply monopolar and/or bipolar RF energy to tissue. In addition, or in the alternative, end effector (230) may include an ultrasonic blade that is operable to apply ultrasonic energy to tissue. In some versions, end effector (230) is operable to apply two or more of monopolar RF energy, bipolar RF energy, or ultrasonic energy to tissue. Other suitable features and functionalities that may be incorporated into end effector (230) will be apparent to those skilled in the art in view of the teachings herein.

Instruments (150, 200) may include a plurality of wires, traces in rigid or flexible circuits, and other electrical features that are in close proximity with each other. Such electrical features may be located within handle assembly (210), within shaft assembly (220), and/or in end effector (230). Such electrical features may also be in close proximity with other components that are not intended to provide pathways for electrical communication but are nevertheless formed of an electrically conductive material. Such electrically conductive mechanical features may include moving components (e.g., drive cables, drive bands, gears, etc.) or stationary components (e.g., chassis or frame members, etc.). This proximity may provide a risk of power or signals undesirably crossing from one electrical feature to another electrical feature and/or from one electrical feature to an electrically conductive mechanical feature, which may cause equipment failure, equipment damage, sensor errors, patient injuries, and/or other undesirable results. In addition, or in the alternative, this proximity may provide a risk of generating electrical potentials between proximate components or creating capacitive couplings between electrical features and/or between an electrical feature and an electrically conductive mechanical feature. Such capacitive coupling may provide undesirable results such as power reductions, signal reductions, signal interference, and/or other undesirable results. It may therefore be desirable to provide features to prevent or otherwise address such occurrences within instruments (150, 200).

III. Further Examples of Surgical Instrument Components

The following description relates to examples of different features that may be incorporated into any of the various instruments (40, 50, 60, 100, 190, 200) described above. While these examples are provided separate from each other, the features described in any of the following examples may be combined with the features described in other examples described below. Thus, the below-described features may be combined in various permutations as will be apparent to those skilled in the art in view of the teachings herein. Similarly, various ways in which the below-described features may be incorporated into any of the various instruments (40, 50, 60, 100, 190, 200) described above will be apparent to those skilled in the art in view of the teachings herein. The below-described features may be incorporated into robotically controlled surgical instruments (40, 50, 60, 190) and/or handheld surgical instruments (100, 200).

A. Example of Ultrasonic End Effector

Figure 5:
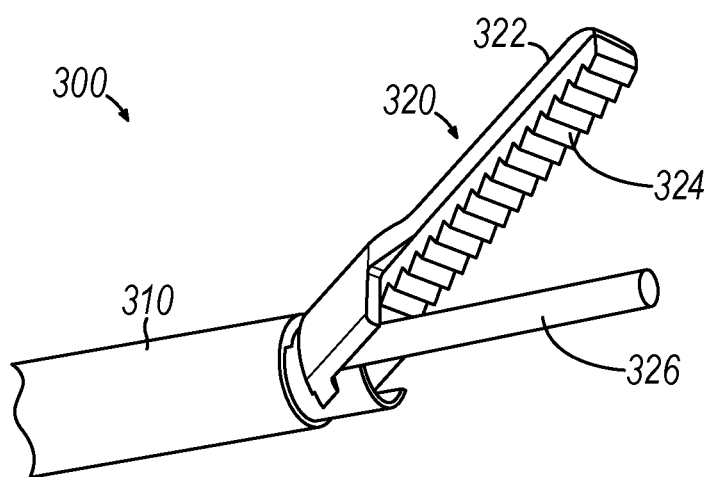
FIG. 5 depicts a perspective view of an example of an end effector that is operable to apply ultrasonic energy to tissue.

FIG. 5 shows a portion of an example of an ultrasonic instrument (300), including a shaft assembly (310) and an end effector (320). End effector (320) includes an upper jaw (322) and an ultrasonic blade (326). Upper jaw (322) is operable to pivot toward ultrasonic blade (326) to thereby compress tissue between a clamp pad (324) of upper jaw (322) and ultrasonic blade (326). When ultrasonic blade (326) is activated with ultrasonic vibrations, ultrasonic blade (326) may sever and seal tissue compressed against clamp pad (324). By way of example only, end effectors (66, 102, 230) may be configured and operable similar to end effector (320).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/ or electrically conductive mechanical features that may provide a risk of generating electrical potentials between proximate components or creating capacitive couplings between electrical features and/or between an electrical feature and an electrically conductive mechanical feature. In the context of instrument (300), such risks may occur with respect to an acoustic waveguide in shaft assembly (310) leading to ultrasonic blade (326), as the acoustic waveguide may be formed of an electrically conductive material. In addition, instrument (300) may include one or more sensors in shaft assembly (310) and/or end effector (320); and may also include one or more electrodes and/or other electrical features in end effector (320). Other components of instrument (350) that may present the above-described risks will be apparent to those skilled in the art in view of the teachings herein.

B. Example of Bipolar RF End Effector

Figure 6:
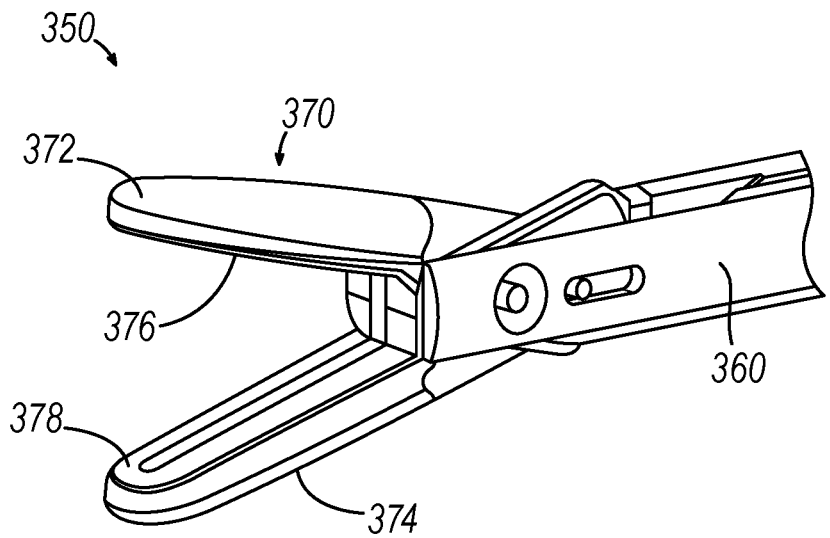
FIG. 6 depicts a perspective view of an example of an end effector that is operable to apply bipolar RF energy to tissue.

FIG. 6 shows a portion of an example of a bipolar RF instrument (350), including a shaft assembly (360) and an end effector (370). End effector (370) includes an upper jaw (372) and a lower jaw (374). Jaws (372, 374) are pivotable toward and away from each other. Upper jaw (372) includes a first electrode surface (376) while lower jaw (374) includes a second electrode surface (378). When tissue is compressed between jaws (372, 374), electrode surfaces (376, 378) may be activated with opposing polarities to thereby apply bipolar RF energy to the tissue. This bipolar RF energy may seal the compressed tissue. In some versions, end effector (370) further includes a translating knife member (not show) that is operable to sever tissue that is compressed between jaws (372, 374). Some variations of end effector (370) may also be operable to cooperate with a ground pad (e.g., ground pad (70)) to apply monopolar RF energy to tissue, such as by only activating one electrode surface (376, 378) or by activating both electrode surfaces (376, 378) at a single polarity. By way of example only, end effectors (64, 102, 230) may be configured and operable similar to end effector (370).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/ or electrically conductive mechanical features that may provide a risk of generating electrical potentials between proximate components or creating capacitive couplings between electrical features and/or between an electrical feature and an electrically conductive mechanical feature. In the context of instrument (350), such risks may occur with respect to electrode surface (376, 378) and the wires or other electrical features that extend along shaft assembly (360) to reach electrode surfaces (376, 378). In addition, instrument (350) may include one or more sensors in shaft assembly (360) and/or end effector (370); and may also include one or more electrodes and/or other electrical features in end effector (370). Other components of instrument (350) that may present the above-described risks will be apparent to those skilled in the art in view of the teachings herein.

C. Example of Monopolar Surgical Instrument Features

Figure 7:
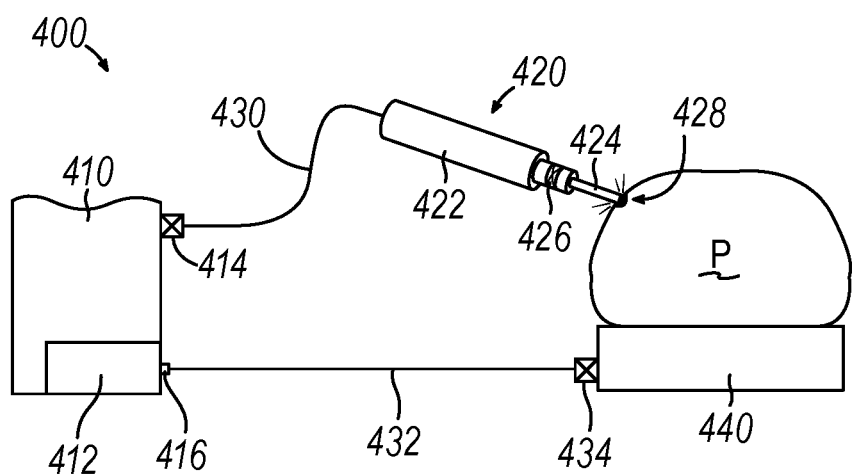
FIG. 7 depicts a schematic view of an example of a surgical instrument that is operable to apply monopolar RF energy to tissue.

FIG. 7 shows an example of a monopolar RF energy delivery system (400) that includes a power generator (410), a delivery instrument (420), and a ground pad assembly (440). In addition to the following teachings, instrument (420) may be constructed and operable in accordance with at least some of the teachings of U.S. Pub. No. 2019/0201077, the disclosure of which is incorporated by reference herein, in its entirety; and/or various other references cited herein. Power generator (410) may be operable to deliver monopolar RF energy to instrument (420) via a cable (430), which is coupled with power generator (410) via a port (414). In some versions, port (414) includes an integral sensor. By way of example only, such a sensor in port (414) may be configured to monitor whether excess or inductive energy is radiating from power generator (410) and/or other characteristics of energy being delivered from power generator (410) via port (414). Instrument (420) includes a body (422), a shaft (424), a sensor (426), and a distal electrode (428) that is configured to contact a patient (P) and thereby apply monopolar RF energy to the patient (P). By way of example only, sensor (426) may be configured to monitor whether excess or inductive energy is radiating from instrument (420). Based on signals from sensor (426), a control module in power generator (410) may passively throttle the ground return from ground pad assembly (440) based on data from sensor (426).

In some versions, ground pad assembly (440) comprises one or more resistive continuity ground pads that provide direct contact between the skin of the patient (P) and one or more metallic components of the ground pad. In some other versions, ground pad assembly (440) comprises a capacitive coupling ground pad that includes a gel material that is interposed between the patient (P) and the ground return plate. In the present example, ground pad assembly (440) is positioned under the patient (P) and is coupled to power generator (410) via a cable (432) via ports (416, 434). Either or both of ports (416, 434) may include an integral sensor. By way of example only, such a sensor in either or both of ports (416, 434) may be configured to monitor whether excess or inductive energy is radiating from ground pad assembly (440).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (420), such risks may occur with respect to sensor (426), distal electrode (428), and/or any other electrical components in instrument (420). Other components of instrument (420) that may present the above-described risks will be apparent to those skilled in the art in view of the teachings herein. Such risks may be greater in versions instrument (420) that are dedicated to providing monopolar RF energy than in the context of bipolar RF instruments such as instrument (350) because a dedicated monopolar RF instrument may lack a ground return path that might otherwise prevent or mitigate the above risks.

D. Example of Articulation Section in Shaft Assembly

Figure 8:
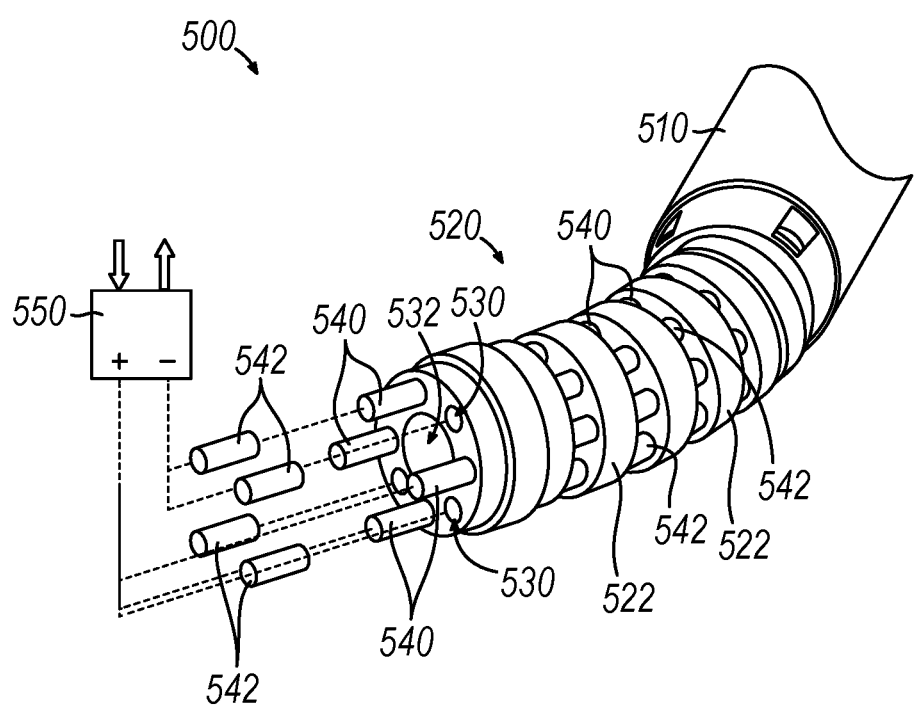
FIG. 8 depicts a perspective view of an example of an articulation section that may be incorporated into a shaft assembly of a surgical instrument.

FIG. 8 illustrates a portion of an instrument (500) that includes a shaft (510) with an articulation section (520). In addition to the following teachings, instalment (500) may be constructed and operable in accordance with at least some of the teachings of U.S. Pub. No. 2017/0202591, now U.S. Pat. No. 11,229,471, the disclosure of which is incorporated by reference herein, in its entirety; and/or various other references cited herein. In the present example, an end effector (550) is positioned at the distal end of articulation section (520). Articulation section (520) includes a plurality of segments (522) and is operable to laterally deflect end effector (550) away from and toward the central longitudinal axis of shaft (510). A plurality of wires (540) extend through shaft (510) and along articulation section (520) to reach end effector (550) and thereby deliver electrical power to end effector (550). By way of example only, end effector (550) may be operable to deliver monopolar and/or bipolar RF energy to tissue as described herein. A plurality of push-pull cables (542) also extend through articulation section (520). Push-pull cables (542) may be coupled with an actuator (e.g., similar to articulation control (218)) to drive articulation of articulation section (520). Segments (522) are configured to maintain separation between, and provide structural support to, wires (540) and push-pull cables (542) along the length of articulation section (520). Articulation section (520) of this example also defines a central passageway (532). By way of example only, central passageway (532) may accommodate an acoustic waveguide (e.g., in variations where end effector (550) further includes an ultrasonic blade), may provide a path for fluid communication, or may serve any other suitable purpose. Alternatively, central passageway (532) may be omitted.

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (500), such risks may occur with respect to wires (540) and/or push-pull cables (542). In addition, instrument (500) may include one or more sensors in shaft assembly (510) and/or end effector (550); and may also include one or more electrodes and/or other electrical features in end effector (550). Other components of instrument (500) that may present the above-described risks will be apparent to those skilled in the art in view of the teachings herein.

E. Example of Wiring to End Effector

Figure 9:
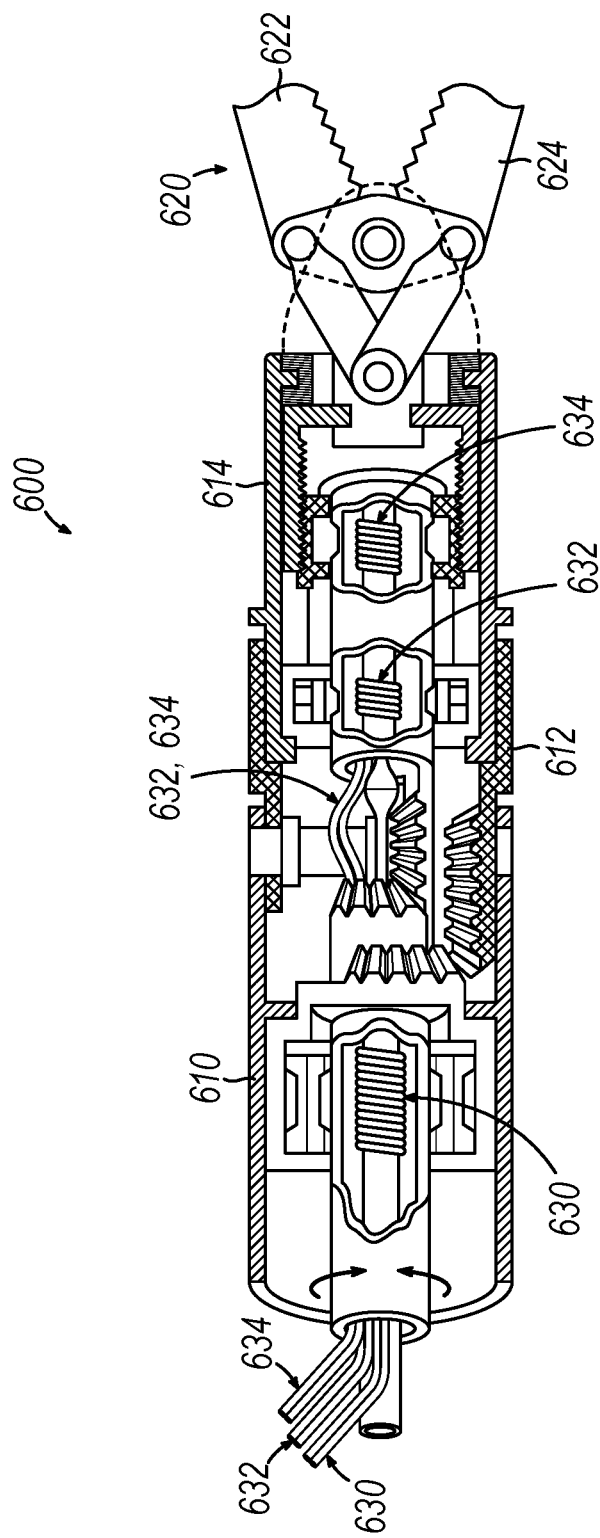
FIG. 9 depicts a side elevation view of a portion of a shaft assembly that may be incorporated into a surgical instrument, with housing components of the shaft being shown in cross-section to reveal internal components of the shaft.

FIG. 9 illustrates a portion of an instrument (600) that includes a shaft (610) with n first articulating segment (612) and a second articulating segment (614). In addition to the following teachings, instalment (600) may be constructed and operable in accordance with at least some of the teachings of U.S. Pub. No. 2017/0202605, entitled "Modular Battery Powered Handheld Surgical Instalment and Methods Therefor," published Jul. 20, 2017, issued as U.S. Pat. No. 10,842,523 on Nov. 24, 2020, the disclosure of which is incorporated by reference herein, in its entirety; and/or various other references cited herein. In the present example, end effector (620) is positioned at the distal end of second articulating segment (614). End effector (620) of this example includes a pair of jaws (622, 624) that are operable to pivot toward and away from each other to grasp tissue. In some versions, one or both of jaws (622, 624) includes one or more electrodes that is/are operable to apply RF energy to tissue as described herein. In addition, or in the alternative, end effector (620) may include an ultrasonic blade and/or various other features. Segments (612, 614) may be operable to pivot relative to shaft (610) and relative to each other to thereby deflect end effector (620) laterally away from or toward the central longitudinal axis of shaft (610).

Instrument (900) of this example further includes a first wire set (630) spanning through shaft (610), a second wire set (632) spanning through shaft (610) and both segments (612, 614), and a third wire set (634) spanning further through shaft (610) and both segments (612, 614). Wire sets (630, 632, 634) may be operable to control movement of segments (612, 614) relative to shaft (610). For instance, power may be communicated along one or more of wire sets (630, 632, 634) to selectively engage or disengage corresponding clutching mechanisms, to thereby allow lateral deflection of one or both of segments (612, 614) relative to shaft (610); and or rotation of one or both of segments (612, 614) relative to shaft (610). Alternatively, power may be communicated along one or more of wire sets (630, 632, 634) to drive corresponding solenoids, motors, or other features to actively drive lateral deflection of one or both of segments (612, 614) relative to shaft (610); and or rotation of one or both of segments (612, 614) relative to shaft (610). In versions where end effector (620) is operable to apply RF energy to tissue, one or more additional wires may extend along shaft (610) and segments (612, 614), in addition to wire sets (630, 632, 634).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (600), such risks may occur with respect to wire sets (630, 632, 634), the electrical components that wire sets (630, 632, 634) are coupled with, and/or other features that drive lateral deflection of one or both of segments (612, 614) relative to shaft (610). In addition, instrument (600) may include one or more sensors in shaft assembly (610) and/or end effector (620); and may also include one or more electrodes and/or other electrical features in end effector (620). Other components of instrument (600) that may present the above-described risks will be apparent to those skilled in the art in view of the teachings herein.

F. Example of Sensors in Shaft Assembly

Figure 10:
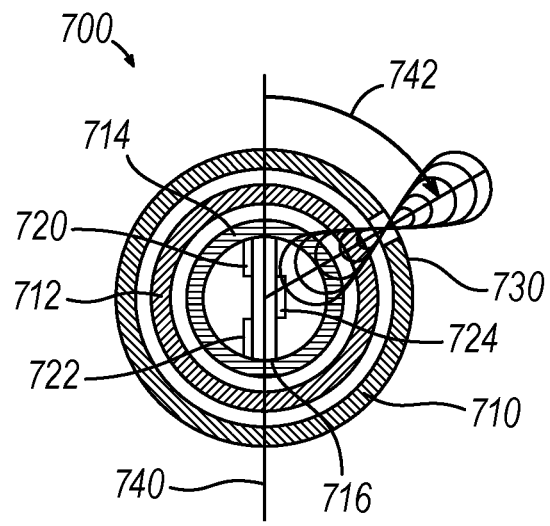
FIG. 10 depicts a cross-sectional end view of another shaft assembly that may be incorporated into a surgical instrument.

FIG. 10 shows an example of another shaft assembly (700) that may be incorporated into any of the various instruments (40, 50, 60, 100, 190, 200, 300, 350, 400, 500, 600) described herein. In addition to the following teachings, shaft assembly (700) may be constructed and operable in accordance with at least some of the teachings of U.S. Pub. No. 2017/0202608, now U.S. Pat. No. 10,835,307, the disclosure of which is incorporated by reference herein, in its entirety; and/or various other references cited herein. Shaft assembly (700) of this example includes an outer shaft (710), a first inner shaft (712), and a second inner shaft (714). A support member (716) spans diametrically across the interior of second inner shaft (714). By way of example only, support member (716) may comprise a circuit board, a flex-circuit, and/or various other electrical components. A plurality of sensors (720, 722, 724) are positioned on support member (716) in the present example. A magnet (730) is embedded in outer shaft (710) which is operable to rotate about inner shafts (712, 714).

In some versions, rotation of outer shaft (710) about inner shafts (712, 714) drives rotation of an end effector (not shown), located at the distal end of shaft assembly (700), about a longitudinal axis of shaft assembly (700). In some other versions, rotation of outer shaft (710) about inner shafts (712, 714) drives lateral deflection of the end effector away from or toward the longitudinal axis of shaft assembly (700). Alternatively, rotation of outer shaft (710) about inner shafts (712, 714) may provide any other results. In any case, sensors (720, 722, 724) may be configured to track the position of magnet (730) and thereby determine a rotational position (742) of outer shaft (710) relative to a fixed axis (740). Thus, sensors (720, 722, 724) may collectively serve as a position sensor like position sensor (112) of instrument (100).

Figure 11:
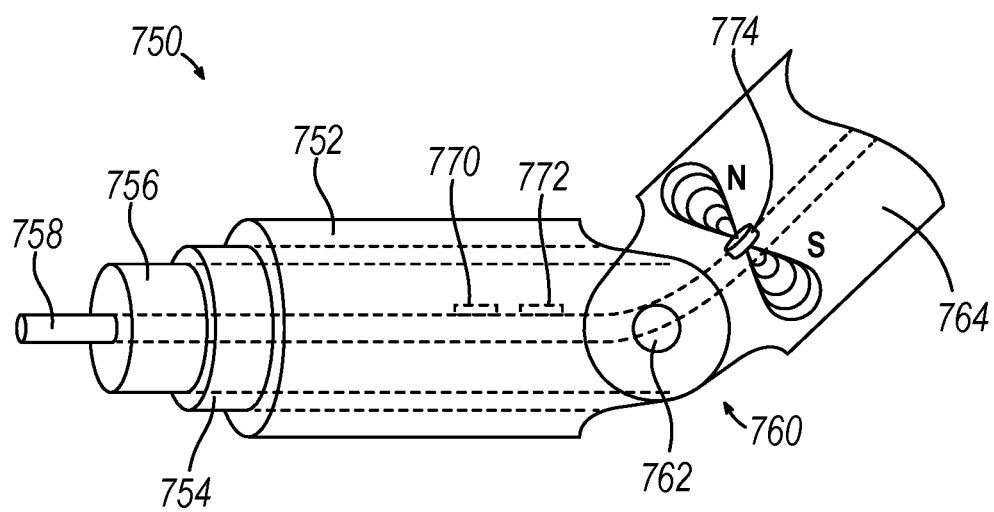
FIG. 11 depicts a schematic view of a portion of another shaft assembly that may be incorporated into a surgical instrument.

FIG. 11 shows an example of another shaft assembly (750) that may be incorporated into any of the various instruments (40, 50, 60, 100, 190, 200, 300, 350, 400, 500, 600) described herein. In addition to the following teachings, shaft assembly (750) may be constructed and operable in accordance with at least some of the teachings of U.S. Pub. No. 2017/0202608, now U.S. Pat. No. 10,835,307, the disclosure of which is incorporated by reference herein, in its entirety; and/or various other references cited herein. Shaft assembly (750) of this example includes a plurality of coaxially positioned proximal shaft segments (752, 754, 756) and a distal shaft segment (764). Distal shaft segment (764) is pivotably coupled with proximal shaft segment (752) via a pin (762) to form an articulation joint (760). An end effector (not shown) may be positioned distal to distal shaft segment (764), such that articulation joint (760) may be utilized to deflect the end effector laterally away from or toward a central longitudinal axis defined by proximal shaft segments (752, 754, 756). A flex circuit (758) spans along shaft segments (752, 754, /56, 764) and is operable to flex as shaft assembly (750) bends at articulation joint (760).

A pair of sensors (770, 772) are positioned along flex circuit (758) within the region that is proximal to articulation joint (760); while a magnet (774) is positioned on flex circuit (758) (or elsewhere within distal shaft segment (764)) in the region that is distal to articulation joint (760). Magnet (774) thus moves with distal shaft segment (764) as distal shaft segment (764) pivots relative to proximal shaft segments (752, 754, 756) at articulation joint (760); while sensors (770, 772) remain stationary during such pivoting. Sensors (770, 772) are configured to track the position of magnet (774) and thereby determine a pivotal position of distal shaft segment (764) relative to proximal shaft segments (752, 754, 756). In other words, sensors (770, 772) and magnet (774) cooperate to enable determination of the articulation bend angle formed by shaft assembly (750). Thus, sensors (770, 772) may collectively serve as a position sensor like position sensor (112) of instrument (100).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instruments (700, 750), such risks may occur with respect to sensors (720, 722, 724, 770, 772), the electrical components that sensors (720, 722, 724, 770, 772) are coupled with, and/or other features within the shaft assemblies of instruments (700, 750). Other components of instruments (700, 750) that may present the above-described risks will be apparent to those skilled in the art in view of the teachings herein.

G. Example of Drive Controls in Body and Shaft Assembly of Instrument

Figure 12:
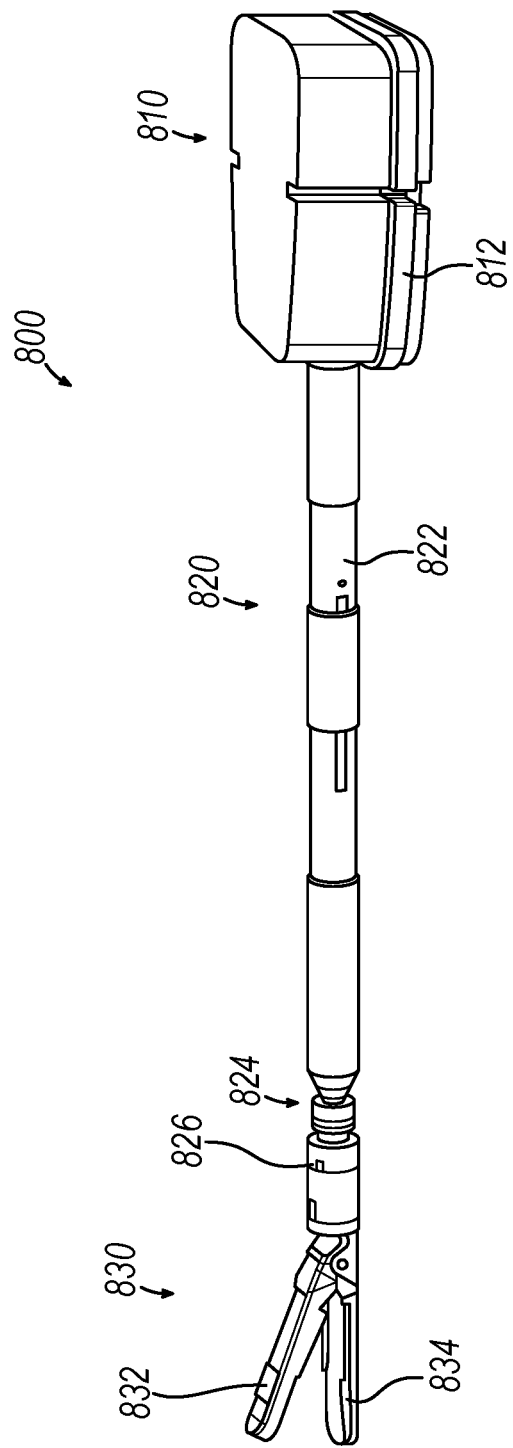
FIG. 12 depicts a perspective view of an example of a surgical instrument that may be incorporated into the robotic surgical system of FIG. 1.
Figure 13:
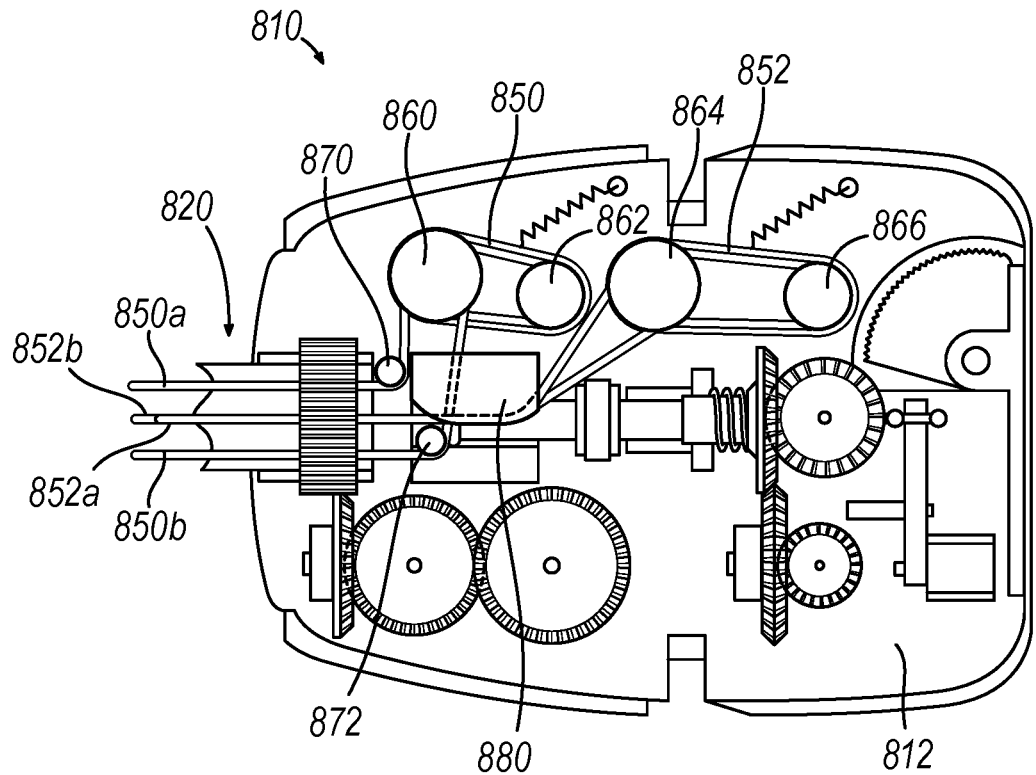
FIG. 13 depicts a top plan view of an interface drive assembly of the instrument of FIG. 12.
Figure 14:
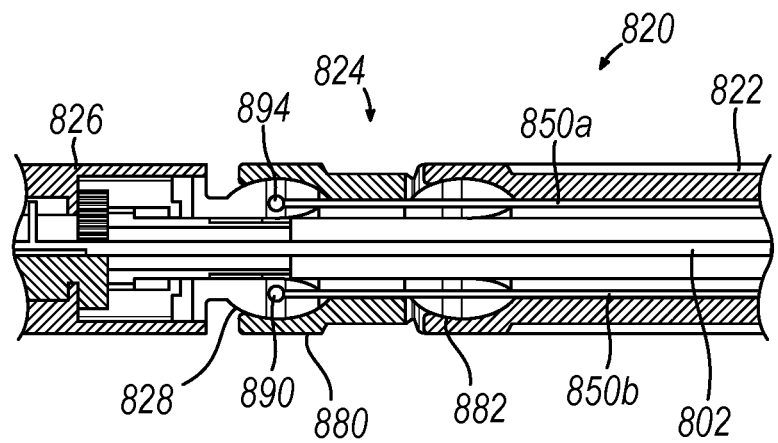
FIG. 14 depicts a cross-sectional side view of an articulation section of a shaft assembly of the instrument of FIG. 12.

FIGS. 12-14 show an example of an instrument (800) that may be incorporated into a robotic surgical system, such as the robotic surgical systems (10, 150) described herein. In addition to the following teachings, instrument (800) may be constructed and operable in accordance with at least some of the teachings of U.S. Pat. No. 9,125,662, the disclosure of which is incorporated by reference herein, in its entirety; and/or various other references cited herein. Instrument (800) of this example includes a body (810), a shaft assembly (820), and an end effector (830). Body (810) includes a base (812) that is configured to couple with a complementary component of a robotic arm (e.g., one of robotic arms (160, 170, 180)). Shaft assembly (820) includes a rigid proximal portion (822), an articulation section (824), and a distal portion (826). End effector (830) is secured to distal portion (826). Articulation section (824) is operable to deflect distal portion (826) and end effector (830) laterally away from and toward the central longitudinal axis defined by proximal portion (822). End effector (830) of this example includes a pair of jaws (832, 834). By way of example only, end effector (830) may be configured and operable like any of the various end effectors (46, 56, 66, 102, 230, 320, 350, 620) described herein.

As shown in FIGS. 13-14, a plurality of drive cables (850, 852) extend from body (810) to articulation section (824) to drive articulation of articulation section (824). Cable (850) is wrapped around a drive pulley (862) and a tensioner (860). Cable (850) further extends around a pair of guides (870, 872), such that cable (850) extends along shaft assembly (820) in two segments (850a, 850b). Cable (852) is wrapped around a drive pulley (866) and a tensioner (864). Cable (852) further extends around a guide (880), such that cable (852) extends along shaft assembly (820) in two segments (852a, 852b). In the present example, each drive pulley (862, 866) is configured to couple with a corresponding drive member (e.g., drive spindle, etc.) of the component of the robotic arm to which base (812) is secured. When drive pulley (862) is rotated, one segment (850a) of cable (850) will translate in a first longitudinal direction along shaft assembly (820); while the other segment (850b) will simultaneously translate in a second (opposite) direction along shaft assembly (820). Similarly, when drive pulley (866) is rotated, one segment (852a) of cable (852) will translate in a first longitudinal direction along shaft assembly (820); while the other segment (852b) will simultaneously translate in a second (opposite) direction along shaft assembly (820).

As shown in FIG. 14, articulation section (824) of the present example includes an intermediate shaft segment (880) that is longitudinally interposed between proximal portion (822) and distal portion (826). A ball feature (828) at the proximal end of distal portion (826) is seated in a socket at the distal end of intermediate shaft segment (880), such that distal portion (826) is operable to pivot relative to intermediate shaft segment (880) along one or more planes. Segments (850a, 850b) of drive cable (850) terminate in corresponding ball-ends (894, 890), which are secured to ball feature (828) of distal portion (822). Drive cable (850) is thus operable to drive pivotal movement of distal portion (826) relative to intermediate shaft segment (880) based on the direction in which drive pulley (862) rotates. A ball feature (882) at the proximal end of intermediate portion (880) is seated in a socket at the distal end of proximal portion (822), such that intermediate portion (880) is operable to pivot relative to proximal portion (822) along one or more planes. In some versions, this pivotal movement of intermediate portion (880) relative to proximal portion (822) is driven by cable (852). As also shown in FIG. 14, an electrical cable (802) passes through articulation section (824). Electrical cable (802) provides a path for electrical communication to end effector (830), thereby allowing for delivery of electrical power (e.g., RF energy) to one or more electrodes in end effector (830), providing a path for electrical signals from one or more sensors in end effector (830) to be communicated back to body (810), and/or other forms of electrical communication.

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (800), such risks may occur with respect to drive cables (850, 852), the components that (850, 852) are coupled with, electrical features within shaft assembly (820), and/or other features within instrument (800). Other components of instrument (800) that may present the above-described risks will be apparent to those skilled in the art in view of the teachings herein.

Figure 15:
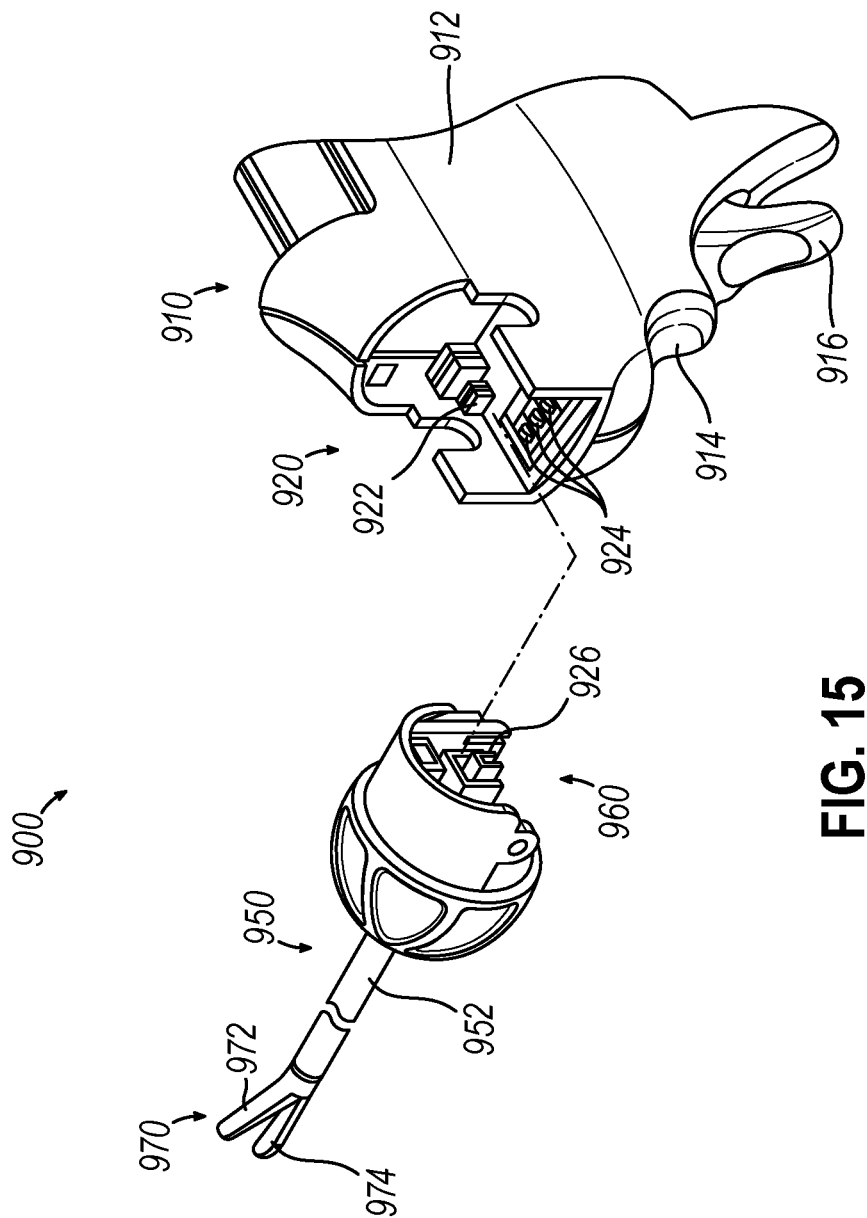
FIG. 15 depicts a perspective view of another example of a handheld surgical instrument, with a modular shaft assembly separated from a handle assembly.

H. Example of Electrical Features at Interface between Modular Components of Instrument In some instances, it may be desirable to provide a surgical instrument that allows for modular coupling and decoupling of components. For instance, FIG. 15 shows an example of an instrument (900) that includes a handle assembly (910) and a modular shaft assembly (950). While instrument (900) of this example is handheld, similar features and modularity may be readily incorporated into a robotically controlled instrument. Handle assembly (910) of this example includes a body (912), an activation button (914), a pivoting trigger (916), and a shaft interface assembly (920). Shaft interface assembly (920) includes a mechanical drive feature (922) and an array of electrical contacts (924). Electrical contacts (924) may be in electrical communication with a control circuit, power source, and/or various other electrical features within handle assembly (910) as will be apparent to those skilled in the art in view of the teachings herein.

Shaft assembly (950) includes a shaft section (952) and an end effector (970), which includes a pair of jaws (972, 874). Shaft section (952) and end effector (970) may be configured and operable in accordance with any of the various shaft assemblies and end effectors described herein. Shaft assembly (950) of this example further includes a handle interface assembly (960). Handle interface assembly (960) includes a mechanical drive feature (962) and a plurality of electrical contacts (not shown). These electrical contacts of handle interface assembly (960) may be in electrical communication with one or more electrodes, sensors, and/or other electrical components within shaft section (952) and/or end effector (970) as will be apparent to those skilled in the art in view of the teachings herein.

When shaft assembly (950) is coupled with handle assembly (910), mechanical drive feature (922) of handle assembly (910) mechanically couples with mechanical drive feature (962) of shaft assembly (950), such that mechanical drive features (922, 962) may cooperate to communicate motion from a motive power source in handle assembly (910) (e.g., pivoting trigger (916), a motor, etc.) to one or more components within shaft section (952) and, in some versions, end effector (970). In some versions, mechanical drive features (922, 962) cooperate to communicate rotary motion from a motive power source in handle assembly (910) (e.g., pivoting trigger (916), a motor, etc.) to one or more components within shaft section (952) and, in some versions, end effector (970). In addition, or in the alternative, mechanical drive features (922, 962) may cooperate to communicate linear translational motion from a motive power source in handle assembly (910) (e.g., pivoting trigger (916), a motor, etc.) to one or more components within shaft section (952) and, in some versions, end effector (970).

When shaft assembly (950) is coupled with handle assembly (910), electrical contacts (924) of shaft interface assembly (920) also couple with complementary electrical contacts of handle interface assembly (960), such that these contacts establish continuity with each other and thereby enable the communication of electrical power, signals, etc. between handle assembly (910) and shaft assembly (950). In addition to or in lieu of having contacts (924), electrical continuity may be provided between handle assembly (910) and shaft assembly (950) via one or more electrical couplings at mechanical drive features (922, 962). Such electrical couplings may include slip couplings and/or various other kinds of couplings as will be apparent to those skilled in the art in view of the teachings herein.

In some scenarios where electrical power or electrical signals are communicated across mating contacts that provide electrical continuity between two components of an instrument (e.g., contacts (924) of shaft interface assembly (920) and complementary electrical contacts of handle interface assembly (960)), there may be a risk of short circuits forming between such contacts. This may be a particular risk when contacts that are supposed to be electrically isolated from each other are located in close proximity with each other, and the area in which these contacts are located may be exposed to fluids during use of the instrument. Such fluid may create electrical bridges between contacts and/or bleed signals that are being communicated between contacts that are supposed to be coupled with each other. It may therefore be desirable to provide features to prevent or otherwise address such occurrences at contacts of an instrument like instrument (900).

In some scenarios where electrical power or electrical signals are communicated across mechanical couplings between different components of an instrument (e.g., via slip couplings, etc.), such couplings might provide variable electrical resistance in a shaft assembly or other assembly of the instrument. For instance, motion at mechanical drive features (922, 962) may provide variable electrical resistance at an electrical slip coupling between mechanical drive features (922, 962); and this variable electrical resistance may impact the communication of electrical power or electrical signals across the slip coupling. This may in turn result in signal loss or power reductions. It may therefore be desirable to provide features to prevent or otherwise address such occurrences at electrical couplings that are found at mechanical couplings between two moving parts of an instrument like instrument (900).

IV. Examples of Electrosurgical System Power Monitoring Features

The following description relates to examples of different features that may be incorporated into any of the various surgical systems described above. Thus, the below-described features may be combined in various permutations as will be apparent to those skilled in the art in view of the teachings herein. Similarly, various ways in which the below-described features may be incorporated into any of the various surgical systems described above will be apparent to those skilled in the art in view of the teachings herein. It should be understood that the below-described features may be incorporated into robotically controlled surgical instruments and/or handheld surgical instruments.

As noted above, some aspects of the present disclosure are presented for a surgical instrument with improved device capabilities for reducing undesired operational side effects. In particular, as described with respect to FIG. 1, some surgical instruments or surgical systems may be configured to apply two or more different types of energy modalities. For example, this may include instruments configured to apply two or more of monopolar RF, bipolar RF, or ultrasonic energy to tissue. Application of two or more energy modalities may in some instances require two or more generators; or in other versions, two or more generator outputs associated with the same generator. However, if two or more energy modalities are used concurrently, the power outputs may induce crosstalk between the generator outputs thereby causing unwanted effects as either instrument contacts the tissue of the patient. Crosstalk may include signal amplification, reduction, interference, or other interactions between the two outputs. It may therefore be desirable to actively monitor one generator output using a monitoring array or generator to provide a second generator a set of energy output parameters. By doing so, the second generator may thereby be capable of outputting an energy signal that does not induce crosstalk between the two or more generator outputs.

Figure 16:
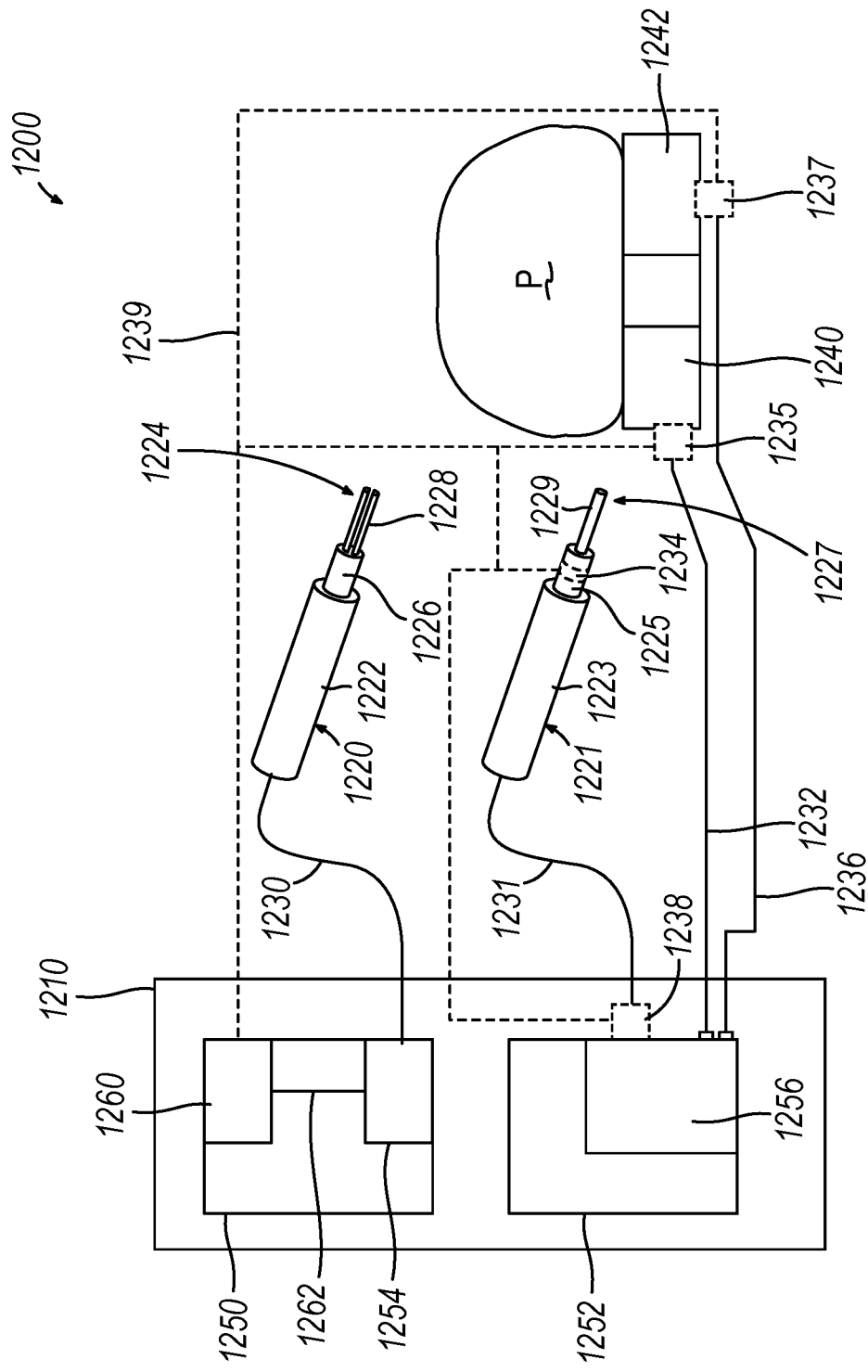
FIG. 16 depicts a schematic view of an example of a dual energy system including instruments that are operable to apply bipolar and monopolar energy to tissue.

FIG. 16 shows one exemplary a dual energy delivery system (1200) that includes a power generator (1210), a first delivery instalment (1220), a second delivery instrument (1221), a first ground pad assembly (1240), and a second ground pad assembly (1242). In addition to the following teachings, instruments (1220. 1221) may be constructed and operable in accordance with at least some of the teachings of U.S. Pub. No. 2019/0201077, issued as U.S. Pat. No. 11,291, 495 on Apr. 5, 2022, the disclosure of which is incorporated by reference herein, in its entirety; and/or various other references cited herein. Power generator (1210) may include a first generator module (1250) and a second generator module (1252), each being operable to deliver different energy modalities via power modules (1254, 1256) to instruments (1220, 1221) via cables (1230, 1231), respectively.

First instrument (1220) may be, for example, a bipolar RF instrument. First instrument (1220) includes a body (1222), a sensor (1226), and an end effector (1224) having a distal electrode assembly (1228) that is configured to contact patient (P) and thereby apply bipolar RF energy to the patient (P). In some versions, electrode assembly (1228) has two electrodes that are positioned to contact tissue simultaneously to thereby deliver bipolar RF energy to the tissue. In some variations, electrode assembly (1228) has more than two electrodes. By way of example only, sensor (1226) may be configured to monitor whether excess or inductive energy is radiating from instrument (1220).

Second instrument (1221) may be, for example, a monopolar RF instrument. Second instrument (1221) also includes a body (1223), a sensor (1225), and an end effector (1227) having a distal electrode (1229) that is configured to contact patient (P) and cooperate with one or more ground pad assemblies (1240, 1242) to apply RF energy to the patient (P). By way of example only, sensor (1225) may be configured to monitor whether excess or inductive energy is radiating from instrument (1220). Based on signals from sensor (1225), a control module in power generator (1210) may passively throttle the ground return from ground pad assemblies (1240, 1242) based on data from sensor (1225). While a bipolar instrument (1220) and a monopolar RF instrument (1221) are described, it should be understood that any two or more instruments may instead be utilized having any two or more energy modalities, such as monopolar RF, bipolar RF, ultrasonic, or any combination thereof.

As shown, a dual ground pad configuration may be utilized for monopolar RF embodiments, comprising two or more resistive continuity ground pads (1240, 1242) that provide direct contact between the skin of the patient (P) and one or more metallic components of the ground pad. In some other versions, ground pad assemblies (1240, 1242) comprise a capacitive coupling ground pad that includes a gel material that is interposed between the patient (P) and a ground return plate. In the present example, ground pad assemblies (1240, 1242) are positioned under the patient (P) and are coupled to power generator (1210) via cables (1232, 1236), respectively.

In some versions of energy delivery system (1200), one or both generator modules (1250, 1252) may include a power monitor such as sensor module (1260). Sensor module (1260) of one generator module (1250) may include a data processor configured to monitor energy present at various points in energy delivery system (1200) that are associated with the instrument (1221) affiliated with the other generator module (1252), particularly output module (1256). Thus, the various measured points showing the energy being output to patient (P) by the second generator module (1252) may be monitored by the first generator module (1250) so that first generator module (1250) may adjust its output parameters to avoid crosstalk.

Sensors (1234, 1235, 1237, 1238) may include, for example, RF power sensors, ammeters, voltmeters, ultrasonic transducers, or other similar power sensing instruments, and may be configured to monitor energy flowing through or radiating from various points being powered by power module (1256), and communicate energy measurements back to sensor module (1260) via communication cable (1239). Particularly, a first sensor (1234) may be positioned on instrument (1221) and may be configured to measure a capacitive coupling energy, a second sensor (1235) may be positioned on return cable (1232) from first ground pad assembly (1240) to monitor energy flowing back to generator module (1252) from patient (P), a third sensor (1237) may be positioned on return cable (1236) from second ground pad assembly (1242) to monitor energy flowing back to generator module (1252) from patient (P), and a fourth sensor (1238) may be positioned on cable (1231) to monitor energy being output from power module (1256) to instrument (1221). While four exemplary sensors (1234, 1235, 1237, 1238) are described at four distinct positions for monitoring energy flowing through or radiating from various points being powered by power module (1256), it should be understood that various other sensor positions have been contemplated and only one or a subset of sensors (1234, 1235, 1237, 1238) may be included in other variations of system (1200).

As described, during operation, sensor module (1260) may monitor signals from any one or more of sensors (1234, 1235, 1237, 1238) to determine the parameters of second output module (1256) to second instrument (1221) and communicate the parameters to first output module (1254) through a data connection (1262). Thereafter, first output module (1254) is configured to adjust its own output energy parameters to first instrument (1220) to avoid outputting too similar of a signal as second output module (1256) is outputting to second instrument (1221). Sensors (1234, 1235, 1237, 1238) may be configured to monitor any energy parameters, such as current, voltage, frequency, power level, and/or wave shape, etc.; and subsequently, first output module (1254) may be configured to adjust those same energy parameters. These adjustments may be made to avoid amplification, cancellation, interference, and/or other interactions between the outputs of output modules (1254, 1256). In other words, second output module (1256) may make ad hoc adjustments, in real time, to automatically adjust the frequency, wave shape, and/or other parameters of its own output to thereby avoid amplification, cancellation, interference, and/or other interactions with the sensed output of first output module (1254). For example, if sensor module (1260) determines that second output module (1256) is outputting a monopolar RF signal of 400 kHz, first output module (1254) may adjust its own bipolar RF output signal to 800 kHz or 1 MHz to adequately distinguish the signals. In some versions, a frequency multiplier circuit (e.g., a two-diode odd-order frequency multiplier, etc.) may be utilized with a single generator output module.

Some generator systems may respond poorly to excessive capacitance in the load. In some instances, this may lead to the generator's tuned circuit output producing higher than expected values of voltage. These higher voltages may exceed the ratings as provided by the generator manufacturer. This overvoltage situation may force the instrument that is being powered by the generator to operate in an out-of-bounds region where the instrument insulation systems are not rated for this higher voltage, which may lead to a potentially dangerous situation where the insulation breaks down and an electric arc is formed. Electric arcs may be highly undesirable in surgery as they may be unpredictable and suddenly burn material around them, thereby releasing chemicals and components that are not intended to be present in the surgical field. The burning of the insulation may further expose conductive surfaces that are not intended to be in contact with the patient. Thus, to prevent or otherwise alleviate these issues, energy delivery system (1200) may be further configured to perform energy parameter adjustments with respect to a time constant, the time constant being based on the natural frequency of the electrical system. Particularly, the time constant is equal to the product of the circuit resistance (in ohms) and the circuit capacitance (in farads).

To perform energy parameter adjustments with respect to the time constant, one or more of sensors (1234, 1235, 1237, 1238) may monitor the capacitive load and the resistive load. The capacitive load may be monitored, for example, by sensor (1234) measuring the parasitic capacitive coupling induced the instrument (1221). The resistive load may be monitored, for example, by a combination of sensors (1234, 1235, 1237, 1238) measuring the tissue load as may be defined by the muscle-to-fat ratio. It should be understood that the measurements and time constant adjustments described above may, in some versions, be performed by the energy delivery system (1200) without the cooperation with either generator module (1250, 1252).

Figure 17:
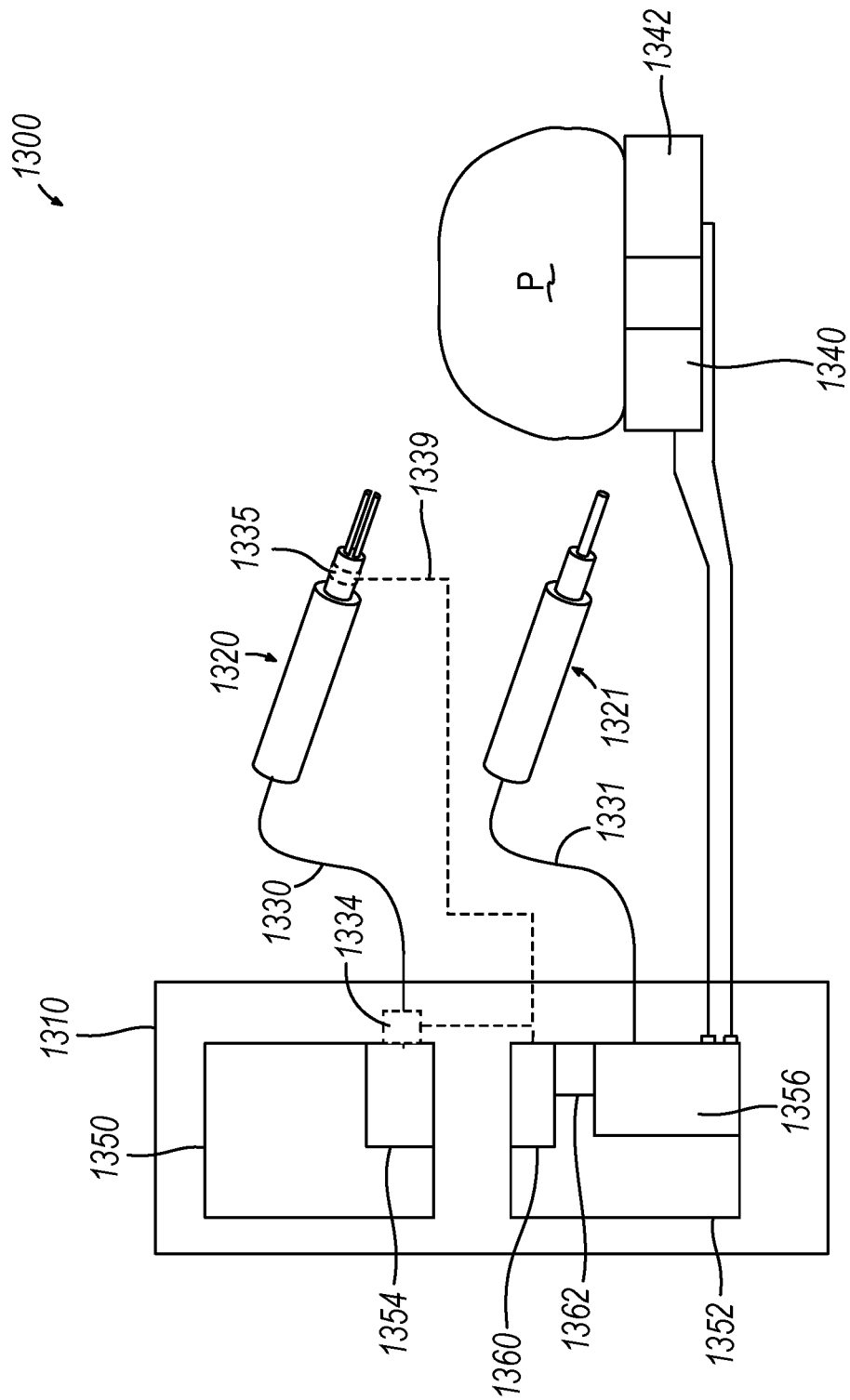
FIG. 17 depicts a schematic view of another example of a dual energy system including instruments that are operable to apply bipolar and monopolar energy to tissue.

FIG. 17 shows an alternative configuration (1300) of energy delivery system (1200). The components and their functionalities of energy delivery system (1300) are the same as described with regard to energy delivery system (1200) except as described below. Particularly, energy delivery system (1300) includes a power generator (1310), a first delivery instrument (1320), a second delivery instrument (1321), a first ground pad assembly (1340), and a second ground pad assembly (1342). Power generator (1310) may include a first generator module (1350) and a second generator module (1352), each being operable to deliver different energy modalities via power modules (1354, 1356) to instruments (1320, 1321) via cables (1330, 1331), respectively. Further, while a bipolar instrument (1320) and a monopolar RF instrument (1321) are described, it should be understood that any two or more instruments may instead be utilized having any two or more energy modalities, such as monopolar RF, bipolar RF, ultrasonic, or any combination thereof.

In this version, generator module (1352) includes a power monitor such as sensor module (1360) that is coupled with power module (1356). Sensor module (1360) of second generator module (1352) may include a data processor configured to monitor energy present at various points in energy delivery system (1300) that are associated with the instrument (1320) affiliated with the other generator module (1350), particularly output module (1354). Thus, the various measured points showing the energy being output to patient (P) by the first generator module (1350) may be monitored by the second generator module (1352) so that second generator module (1352) may adjust its output parameters to avoid crosstalk. Sensors (1334, 1335) may include, for example, RF power sensors, ammeters, voltmeters, ultrasonic transducers, or other similar power sensing instruments; and may be configured to monitor energy flowing through or radiating from various points being powered by power module (1354) and communicate energy measurements back to sensor module (1360) via communication cable (1339). Particularly, a first sensor (1334) may be positioned at the output of power module (1354) and may be configured to measure the output energy signal provided to power instrument (1320); while a second sensor (1335) may be positioned on instrument (1320) and may be configured to measure a capacitive coupling energy. While two exemplary sensors (1334, 1335) are described at two distinct positions for monitoring energy flowing through or radiating from various points being powered by power module (1354), it should be understood that various other sensor positions have been contemplated and only one or a subset of sensors (1334, 1335) may be included.

As described, during operation, sensor module (1360) may monitor any one of sensors (1334, 1335) to determine the parameters of first output module (1354) to first instrument (1320) and communicate the parameters to second output module (1356) through a data connection (1362). Thereafter, second output module (1356) is configured to adjust its own output energy parameters to second instrument (1321) to avoid outputting too similar of a signal as first output module (1354) is outputting to first instrument (1320). Sensors (1334, 1335) may be configured to monitor any energy parameters, such as current, voltage, frequency, power level, and/or wave shape, etc.; and subsequently, second output module (1354) may be configured to adjust those same energy parameters. These adjustments may be made to avoid amplification, cancellation, interference, and/or other interactions between the outputs of output modules (1354, 1356). In other words, second output module (1356) may make ad hoc adjustments, in real time, to automatically adjust the frequency, wave shape, and/or other parameters of its own output to thereby avoid amplification, cancellation, interference, and/or other interactions with the sensed output of first output module (1354). For example, if sensor module (1360) determines that first output module (1354) is outputting a monopolar RF signal of 400 kHz, second output module (1356) may adjust its own bipolar RF output signal to 800 kHz or 1 MHz to adequately distinguish the signals. In some versions, a frequency multiplier circuit (e.g., a two-diode odd-order frequency multiplier, etc.) may be utilized with a single generator output module.

While the foregoing examples shown in FIGS. 16-17 have been shown in the context of handheld instruments (1220, 1221, 1320, 1321), the same teachings may be readily applied in the context of robotically controlled instruments, including but not limited to robotically controlled instruments as described above and as described in various references cited herein. Similarly, while the foregoing examples shown in FIGS. 16-17 have been shown in the context of external generators (1210, 1310) that are coupled with instruments (1220, 1221, 1320, 1321) via cables (1230, 1231, 1330, 1331), the same teachings may be readily applied in the context of instruments having integral generators (1210, 1310) contained within the body of the instrument. An example of such a scenario may include an instrument having an end effector that is operable to apply two or more kinds of energy modalities (e.g., monopolar RF, bipolar RF, ultrasonic, etc.), with two or more corresponding kinds of generators contained within the body of the instrument to drive those two or more energy modalities.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical system, comprising: (a) a first instrument having a first end effector, wherein the first end effector is operable to apply a first type of energy to tissue of a patient; (b) a second instrument having a second end effector, wherein the second end effector is operable to apply a second type of energy to tissue of a patient; (c) one or more electric power generators configured to generate first and second energy signals, wherein the one or more electric power generators include: (i) a first generator output configured to transmit the first energy signal to the first end effector, wherein the first energy signal is operable to power the first end effector to apply the first type of energy to tissue of a patient, and (ii) a second generator output configured to transmit the second energy signal to the second end effector, wherein the second energy signal is operable to power the second end effector to apply the second type of energy to tissue of a patient; and (d) a power monitor operatively coupled with the one or more electric power generators, wherein the power monitor is configured to monitor a first energy parameter of the first energy signal and transmit the first energy parameter to the one or more electric power generators, wherein the one or more electric power generators is configured to adjust a second energy parameter of the second energy signal, based at least in part on the transmitted first energy parameter, to avoid interactions between the first energy signal and the second energy signal.

Example 2

The surgical system of Example 1, wherein the one or more electric generators are configured to generate the first and second energy signals simultaneously.

Example 3

The surgical system of any one or more of Examples 1 through 2, wherein first and second energy parameters each include at least one of electrical current, voltage, frequency, or wave shape.

Example 4

The surgical system of any one or more of Examples 1 through 3, wherein the first and second end effectors include at least one of a monopolar RF electrode, bipolar RF electrodes, or an ultrasonic blade.

Example 5

The surgical system of any one or more of Examples 1 through 4, further comprising one or more power sensors operatively coupled with the power monitor, wherein the one or more power sensors are configured to measure the first energy parameter and transmit the measurement to the power monitor.

Example 6

The surgical system of Example 5, wherein one or more power sensors includes at least one of an RF power sensor or an ultrasonic transducer.

Example 7

The surgical system of any one or more of Examples 5 through 6, wherein the first instrument includes a monopolar RF instrument with a conductive component, wherein the conductive component is configured to collect a capacitive coupling current that is induced by application of the first energy signal to the first end effector, wherein the one or more power sensors is configured to measure the capacitive coupling current and provide a current measurement to the power monitor.

Example 8

The surgical system of Example 7, wherein the power monitor is configured to transmit the current measurement to the one or more electric power generators, wherein the one or more electric power generators is configured to adjust a time constant parameter of the second energy signal.

Example 9

The surgical system of any one or more of Examples 1 through 8, wherein the first and second instruments are each handheld surgical instruments.

Example 10

The surgical system of any one or more of Examples 1 through 9, wherein the first and second instruments are each components of a robotic electrosurgical system.

Example 11

The surgical system of any one or more of Examples 1 through 10, the one or more electric power generators including a first power generator and a second power generator, the first generator output being part of the first power generator, the second power output being part of the second power generator.

Example 12

The surgical system of any one or more of Examples 1 through 11, the first type of energy including electrosurgical energy.

Example 13

The surgical system of Example 12, the first type of energy including monopolar RF electrosurgical energy, the second type of energy including bipolar RF electrosurgical energy.

Example 14

The surgical system of any one or more of Examples 12 through 13, further comprising a ground pad, the ground pad being configured to contact skin of a patient, the ground pad being further configured to couple with the one or more electric power generator to thereby provide a ground return path.

Example 15

The surgical system of any one or more of Examples 1 through 14, the second energy parameter including a frequency based energy parameter.

Example 16

A surgical system, comprising: (a) a first instrument having a first end effector, wherein the first end effector is operable to apply a first type of energy to tissue of a patient; (b) a second instrument having a second end effector, wherein the second end effector is operable to apply a second type of energy to tissue of a patient; (c) a first generator configured to generate a first energy signal and to transmit the first energy signal to the first end effector, wherein the first energy signal is operable to power the first end effector, and (d) a second generator configured to generate a second energy signal and to transmit the second energy signal to the second end effector, wherein the second energy signal is operable to power the second end effector, and (e) a power monitor operatively coupled with the first and generators, wherein the power monitor is configured to monitor the first energy signal of the first generator and transmit a corresponding measurement signal to the second generator, wherein the second generator is configured to adjust an energy parameter of the second energy signal in response to receiving the transmitted measurement signal.

Example 17

The surgical system of Example 16, wherein the second generator is configured to adjust the energy parameter to distinguish the energy parameter of the second energy signal from a corresponding energy parameter of the first energy signal, based at least in part on the transmitted measurement signal, to avoid interactions between the first energy signal and the second energy signal.

Example 18

The surgical system of any one or more of Examples 16 through 17, wherein the power monitor is configured to monitor one or more of an electrical current, voltage, frequency, or wave shape of the first energy signal of the first generator, wherein the transmitted measurement signal is associated with the monitored one or more of electrical current, voltage, frequency, or wave shape of the first energy signal.

Example 19

The surgical system of any one or more of Examples 16 through 18, wherein the first and second generators are configured to generate the first and second energy signals simultaneously.

Example 20

The surgical system of any one or more of Examples 16 through 19, wherein the first and second end effectors each include at least one of a monopolar RF electrode, bipolar RF electrodes, or an ultrasonic blade.

Example 21

The surgical system of any one or more of Examples 16 through 20, further comprising one or more sensors operatively coupled with the power monitor, wherein the one or more sensors are configured to measure the one or more corresponding energy parameters of the first energy signal of the first generator.

Example 22

The surgical system of Example 21, wherein one or more sensors includes at least one of an RF power sensor or an ultrasonic transducer.

Example 23

The surgical system of any one or more of Examples 16 through 22, wherein the first instrument includes a monopolar RF instrument having a conductive component, wherein the conductive component is configured to collect a capacitive coupling current that is induced by application of the first energy signal to the first end effector, the system further comprising one or more sensors configured to measure the capacitive coupling current and provide a current measurement to the power monitor.

Example 24

The surgical system of Example 23, wherein the power monitor is configured to transmit the current measurement to the second generator, wherein the second generator is configured to adjust a time constant parameter of the second energy signal.

Example 25

A method for performing an electrosurgical procedure, comprising: (a) generating a first energy signal having a first frequency for powering a first end effector of a surgical instrument, wherein the first end effector applies a first type of energy to tissue of a patient; (b) generating a second energy signal having a second frequency for simultaneously powering a second end effector of a surgical instrument, wherein the second end effector applies a second type of energy to tissue of the patient; (c) measuring the first frequency of the first energy signal; (d) based upon the measurement of the frequency of the first energy signal, adjusting the second frequency of the second energy signal to distinguish the second frequency from the first frequency so as to prevent the second energy signal from interacting with the first energy signal.

VI. Miscellaneous

Versions of the devices described above may have application in conventional medical treatments and procedures conducted by a medical professional, as well as application in robotic-assisted medical treatments and procedures.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent Ser. No. 17/136,137, entitled "Filter for Monopolar Surgical Instrument Energy Path," filed on Dec. 29, 2020, and published as U.S. Pub. No. 2022/0202474 on Jun. 30, 2022, the disclosure of which is incorporated by reference herein. Various suitable ways in which the teachings herein may be combined with the teachings of U.S. patent application Ser. No. 17/136,137 (U.S. Pub. No. 2022/0202474) will be apparent to those of ordinary skill in the art in view of the teachings herein.

In addition to the foregoing, the teachings herein may be readily combined with the teachings of U.S. patent application Ser. No. 17/136,139, entitled "Electrosurgical Instrument System with Parasitic Energy Loss Monitor," filed on Dec. 29, 2020, and published as U.S. Pub. No. 2022/0202470 on Jun. 30, 2022, the disclosure of which is incorporated by reference herein. Various suitable ways in which the teachings herein may be combined with the teachings of U.S. patent application Ser. No. 17/136,139 (U.S. Pub. No. 2022/0202470) will be apparent to those of ordinary skill in the art in view of the teachings herein.

In addition to the foregoing, the teachings herein may be readily combined with the teachings of U.S. patent application Ser. No. 17/136,145, entitled "Electrosurgical Instalment with Shaft Voltage Monitor," filed on Dec. 29, 2020, and published as U.S. Pub. No. 2022/0202487 on Jun. 30, 2022, the disclosure of which is incorporated by reference herein. Various suitable ways in which the teachings herein may be combined with the teachings of U.S. patent application Ser. No. 17/136,145 (U.S. Pub. No. 2022/0202487) will be apparent to those of ordinary skill in the art in view of the teachings herein.

In addition to the foregoing, the teachings herein may be readily combined with the teachings of U.S. patent application Ser. No. 17/136,154, entitled "Electrosurgical Instalment with Electrical Resistance Monitor at Rotary Coupling," filed on Dec. 29, 2020, and published as U.S. Pub. No. 2022/0202476 on Jun. 30, 2022, the disclosure of which is incorporated by reference herein. Various suitable ways in which the teachings herein may be combined with the teachings of U.S. patent application Ser. No. 17/136,154 (U.S. Pub. No. 2022/0202476) will be apparent to those of ordinary skill in the art in view of the teachings herein.

In addition to the foregoing, the teachings herein may be readily combined with the teachings of U.S. patent application Ser. No. 17/136,158, entitled "Electrosurgical Instrument with Modular Component Contact Monitoring," filed on even date herewith Dec. 29, 2020, and published as U.S. Pub. No. 2022/0202488 on Jun. 30, 2022, the disclosure of which is incorporated by reference herein. Various suitable ways in which the teachings herein may be combined with the teachings of U.S. patent application Ser. No. 17/136,158 (U.S. Pub. No. 2022/0202488) will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical system, comprising:
(a) a first instrument having a first end effector, wherein the first end effector is operable to apply a first type of energy to tissue of a patient;
(b) a second instrument having a second end effector, wherein the second end effector is operable to apply a second type of energy to tissue of a patient;
(c) at least one electric power generator configured to generate first and second energy signals, wherein the at least one electric power generator includes:
(i) a first generator output configured to transmit the first energy signal to the first end effector, wherein the first energy signal is operable to power the first end effector to apply the first type of energy to tissue of a patient, and
(ii) a second generator output configured to transmit the second energy signal to the second end effector, wherein the second energy signal is operable to power the second end effector to apply the second type of energy to tissue of a patient; and
(d) a power monitor operatively coupled with the at least one electric power generator, wherein the power monitor is configured to monitor a first energy parameter and a second energy parameter of the first energy signal at different locations along a path of the first energy signal and transmit the first energy parameter and the second energy parameter to the at least one electric power generator, wherein the at least one electric power generator is configured to adjust the second energy signal, based at least in part on the transmitted first energy parameter and the transmitted second energy parameter, to avoid interactions between the first energy signal and the second energy signal.

2. The surgical system of claim 1, wherein the at least one electric power generator is configured to generate the first and second energy signals simultaneously.

3. The surgical system of claim 1, wherein the first and second energy parameters each include at least one of electrical current, voltage, frequency, or wave shape.

4. The surgical system of claim 1, wherein the first and second end effectors include at least one of a monopolar RF electrode, bipolar RF electrodes, or an ultrasonic blade.

5. The surgical system of claim 1, further comprising one or more power sensors operatively coupled with the power monitor, wherein the one or more power sensors are configured to measure the first energy parameter and the second energy parameter and transmit the measurements to the power monitor.

6. The surgical system of claim 5, wherein the one or more power sensors includes at least one of an RF power sensor or an ultrasonic transducer.

7. The surgical system of claim 5, wherein the first instrument includes a monopolar RF instrument with a conductive component, wherein the conductive component is configured to collect a capacitive coupling current that is induced by application of the first energy signal to the first end effector, wherein the one or more power sensors is configured to measure the capacitive coupling current and provide a current measurement to the power monitor.

8. The surgical system of claim 7, wherein the power monitor is configured to transmit the current measurement to the at least one or more electric power generator, wherein the at least one electric power generator is configured to adjust a time constant parameter of the second energy signal.

9. The surgical system of claim 1, wherein the first and second instruments are each handheld surgical instruments.

10. The surgical system of claim 1, wherein the first and second instruments are each components of a robotic electrosurgical system.

11. The surgical system of claim 1, the at least one electric power generator including a first power generator and a second power generator, the first generator output being part of the first power generator, the second power output being part of the second power generator.

12. The surgical system of claim 1, the first type of energy including electrosurgical energy.

13. The surgical system of claim 12, the first type of energy including monopolar RF electrosurgical energy, the second type of energy including bipolar RF electrosurgical energy.

14. The surgical system of claim 12, further comprising a ground pad, the ground pad being configured to contact skin of a patient, the ground pad being further configured to couple with the at least one electric power generator to thereby provide a ground return path.

15. The surgical system of claim 1, wherein the at least one electric power generator is configured to adjust a frequency based energy parameter of the second energy signal based at least in part on the transmitted first energy parameter and the transmitted second energy parameter.

16. A surgical system, comprising:
(a) a first instrument having a first end effector, wherein the first end effector is operable to apply a first type of energy to tissue of a patient;
(b) a second instrument having a second end effector, wherein the second end effector is operable to apply a second type of energy to tissue of a patient;
(c) a first generator configured to generate a first energy signal and to transmit the first energy signal to the first end effector, wherein the first energy signal is operable to power the first end effector, and
(d) a second generator configured to generate a second energy signal and to transmit the second energy signal to the second end effector, wherein the second energy signal is operable to power the second end effector, and
(e) a power monitor operatively coupled with the first and generators, wherein the power monitor is configured to monitor the first energy signal of the first generator and transmit corresponding first and second measurement signals to the second generator from different locations along a path of the first energy signal, wherein the second generator is configured to adjust an energy parameter of the second energy signal in response to receiving the transmitted first and second measurement signals.

17. The surgical system of claim 16, wherein the second generator is configured to adjust the energy parameter to distinguish the energy parameter of the second energy signal from a corresponding energy parameter of the first energy signal, based at least in part on the transmitted first and second measurement signals, to avoid interactions between the first energy signal and the second energy signal.

18. The surgical system of claim 16, wherein the power monitor is configured to monitor one or more of an electrical current, voltage, frequency, or wave shape of the first energy signal of the first generator, wherein the transmitted first and second measurement signals are associated with the monitored one or more of electrical current, voltage, frequency, or wave shape of the first energy signal.

19. The surgical system of claim 16, wherein the first instrument includes a monopolar RF instrument having a conductive component, wherein the conductive component is configured to collect a capacitive coupling current that is induced by application of the first energy signal to the first end effector, the system further comprising one or more sensors configured to measure the capacitive coupling current and provide a current measurement to the power monitor, wherein the power monitor is configured to transmit the current measurement to the second generator, wherein the second generator is configured to adjust a time constant parameter of the second energy signal.

20. A surgical system, comprising:
(a) a first instrument having a first end effector, wherein the first end effector is operable to apply a first type of energy to tissue of a patient;
(b) a second instrument having a second end effector, wherein the second end effector is operable to apply a second type of energy to tissue of a patient;
(c) a first power generator module configured to transmit a first energy signal to the first end effector, wherein the first energy signal is operable to power the first end effector to apply the first type of energy to tissue of a patient;
(d) a second power generator module configured to transmit a second energy signal to the second end effector, wherein the second energy signal is operable to power the second end effector to apply the second type of energy to tissue of a patient; and (e) a power monitor operatively coupled with the first power generator module, wherein the power monitor is configured to monitor a first energy parameter and a second energy parameter of the second energy signal at different locations along a path of the second energy signal and, wherein the first power generator module is configured to adjust the first energy signal, based at least in part on the first energy parameter and the second energy parameter to avoid interactions between the first energy signal and the second energy signal.

\* \* \* \* \*